US012611181B2

(12) United States Patent
Sklenar et al.

(10) Patent No.: US 12,611,181 B2
(45) Date of Patent: Apr. 28, 2026

(54) METHODS FOR DISPLAYING REPLENISHMENT TIME DATA USING MYOCARDIAL CONTRAST ECHOCARDIOGRAPHY AND RELATED SYSTEMS

(71) Applicant: narnar, LLC, Lake Oswego, OR (US)

(72) Inventors: Jiri Sklenar, Lake Oswego, OR (US);
David Sklenar, Lake Oswego, OR (US)

(73) Assignee: Narnar, LLC, Lake Oswego, OR (US)

( * ) Notice: Subject to any disclaimer, the term of this patent is extended or adjusted under 35 U.S.C. 154(b) by 39 days.

(21) Appl. No.: 18/750,998

(22) Filed: Jun. 21, 2024

(65) Prior Publication Data

US 2024/0423591 A1     Dec. 26, 2024

Related U.S. Application Data

(60) Provisional application No. 63/510,009, filed on Jun. 23, 2023.

(51) Int. Cl.
A61B 8/08          (2006.01)
A61B 8/00          (2006.01)
A61B 8/06          (2006.01)

(52) U.S. Cl.
CPC ............... A61B 8/481 (2013.01); A61B 8/06 (2013.01); A61B 8/4488 (2013.01); A61B 8/463 (2013.01); A61B 8/5223 (2013.01); A61B 8/54 (2013.01)

(58) Field of Classification Search
CPC ......... A61B 8/481; A61B 8/06; A61B 8/4488; A61B 8/463; A61B 8/5223; A61B 8/54;
(Continued)

(56) References Cited

U.S. PATENT DOCUMENTS 6,315,730 B1     11/2001   Hoff et al.
6,692,438 B2     2/2004    Skyba et al.
(Continued)

OTHER PUBLICATIONS

Myronenko et al., "Point-Set Registration: Coherent Point Drift," IEEE Trans. on Pattern Analysis and Machine Intelligence, vol. 32, issue 12, pp. 2262-2275 (May 15, 2009).
(Continued)

*Primary Examiner* — Kaitlyn E Sebastian
(74) *Attorney, Agent, or Firm* — Kolitch Romano Dascenzo Gates LLP

(57)          ABSTRACT

Methods for displaying blood replenishment time in a tissue may include determining a respective initial video intensity for each respective pixel of a plurality of pixels of an ultrasound image, determining a respective subsequent video intensity of each respective pixel at a plurality of subsequent timepoints, and using the data to determine a respective steady-state concentration of microbubbles in the blood volume, blood velocity, and time-to-target-replenishment for each respective pixel. The time-to-target-replenishment may be color-coded for each respective pixel using a colormap that assigns a first color to respective times-to-target-replenishment that are below a predetermined threshold time, and a second color to respective times-to-target-replenishment that are above the predetermined threshold time. An output image may then be created that displays the plurality of pixels color-coded according to the time-to-target-replenishment, thereby differentiating between portions of the tissue experiencing respective times-to-target-replenishment that are above and below the predetermined threshold time.

20 Claims, 12 Drawing Sheets
(7 of 12 Drawing Sheet(s) Filed in Color)

(58) Field of Classification Search
        CPC ....... A61B 8/065; A61B 8/0883; A61B 8/085;
                                            A61B 8/0891
        See application file for complete search history.

(56)                     References Cited

U.S. PATENT DOCUMENTS

| | | | |
|---|---|---|---|
| 7,931,595 | B2 | 4/2011 | Bendiksen et al. |
| 8,036,437 | B2 | 10/2011 | Arditi et al. |
| 2002/0040189 | A1* | 4/2002 | Averkiou ............ G01S 7/52026 |
| | | | 600/458 |
| 2004/0066389 | A1 | 4/2004 | Skyba et al. |
| 2007/0055161 | A1 | 3/2007 | Garg et al. |
| 2022/0398725 | A1* | 12/2022 | Wang .................... A61B 8/481 |

OTHER PUBLICATIONS

Salgo, S. Ivan, Product specification "Clinical benefits of QLAB software for advanced 2D and 3D echo quantification," Philips Medical Systems (Aug. 2006).
Wei et al., "Quantification of Myocardial Blood Flow witth Ultrasound-Induced Destruction of Microbubbles Administered as a Constant Venous Infusion," Basic Science Reports, vol. 97, issue 5, pp. 473-483 (Feb. 10, 1998).

* cited by examiner

METHODS FOR DISPLAYING REPLENISHMENT TIME DATA USING MYOCARDIAL CONTRAST ECHOCARDIOGRAPHY AND RELATED SYSTEMS

RELATED APPLICATION

The present application claims priority to U.S. Provisional Patent Application No. 63/510,009, filed Jun. 23, 2023, and entitled METHODS FOR DISPLAYING REPLENISH-MENT TIME DATA USING MYOCARDIAL CONTRAST ECHOCARDIOGRAPHY AND RELATED SYSTEMS. The complete disclosure of which is hereby incorporated by reference.

FIELD

This disclosure relates to ultrasonic imaging for diagnostic purposes. More particularly, this disclosure relates to methods of performing myocardial contrast echocardiography (MCE) to visualize parameters such as replenishment time of blood in the myocardium, as well as systems implementing the same.

BACKGROUND

Ultrasonic imaging, or an ultrasound scan, is used for visualization and diagnostics within a body via transmission of ultrasonic waves into the body through the surface of the skin. The ultrasonic waves are reflected back from tissues and cells within the body, received by an ultrasonic transducer, and processed to produce an image (e.g., a sonogram). Ultrasonic contrast agents (which may also be referred to as ultrasound enhancing agents), such as gas-filled microbubbles, are sometimes used to improve ultrasonic diagnosis. Commercially available microbubbles may be introduced intravenously to the circulatory system of a patient's body. Because the microbubbles reflect ultrasonic waves more strongly than do soft tissues and fluids of the body, use of contrast agents such as microbubbles enhance the contrast of the ultrasound. The microbubbles remain in the intravascular compartment, where they behave like red blood cells, which makes them ideal tracers of blood flow. Contrast-enhanced ultrasound can be used to enhance tissue-blood boundaries (e.g., the endocardium of the left ventricle), image blood perfusion in organs, measure blood-flow rate in the heart and other organs, and for other applications.

In the specific field of myocardial contrast echocardiography (MCE), ultrasounds enhanced using intravenous microbubbles have been used to assess replenishment of blood within the myocardium. In practice, the microbubbles are introduced intravenously into the body, and they then pass with the blood through capillaries. While ultrasound techniques can only image tissues (and not blood), the introduction of microbubbles to the circulatory system enables visualization of the blood while the microbubbles are present in the blood. The microbubbles in the myocardium are then destroyed with one or more high-energy ultrasound pulses, and fresh blood that flows back into the myocardium (replenishment) can be imaged as non-destroyed microbubbles re-enter the myocardium from the bloodstream, thereby providing a functional assessment of the myocardium. MCE has been used for detecting perfusion abnormalities related to ischemia at rest or during stress from coronary artery disease, for differentiation of coronary artery disease (CAD) from other conditions that can produce similar symptoms (e.g., EKG abnormalities, cardiomyopathy, myocarditis), to spatially evaluate the presence of myocardial viability for the determination of the success and extent of microvascular reperfusion after urgent revascularization, for diagnosing the syndrome of ischemia in the presence of no or non-obstructive CAD (INOCA), and for differentiation between thrombus and tumor in patients with cardiac masses. The potential benefits of MCE are not only its low cost and wide availability, but also its ability to be performed repetitively to assess response to therapy without exposure to the ionizing radiation that may occur with other techniques. However, MCE has been met with relatively limited adoption, due to technical demands which require specialized training, and lack of quantification software to provide support to clinicians interpreting the images.

SUMMARY

Presently disclosed methods may address one or more limitations with prior art techniques, such as those discussed above, by analyzing and displaying data from myocardial contrast echocardiography to help physicians or researchers visually assess for normal and abnormal perfusion in the myocardium or other tissues of the body. Generally, according to presently disclosed methods, ultrasonic contrast agents are used to highlight the presence of blood in tissue and assess how quickly blood refills, or replenishes, in different areas of the tissue. Video brightness data is collected from respective pixels and/or from a grid of pixels surrounding the respective pixel. Curve fitting is performed to determine a steady-state concentration of microbubbles in the blood volume and a blood velocity for each location of the tissue (as represented by each pixel or group of pixels of the ultrasound image of the tissue), which may be used to provide a simplified output image to indicate whether the imaged area refilled with blood in less than a specific, predetermined threshold amount of time, such as 5 seconds or 2 seconds. The replenishment information may be presented in a single output parametric image and in an intuitive and clinically-relevant way. In the output image, each pixel is color-coded so that practitioners (i.e., physicians, clinicians, technicians, or other users) can get a summary for a whole region of the imaged tissue. The output image may be configured to quickly impart relevant diagnostic information without requiring complex interpretation. In some examples, other parameters can be displayed such as blood flow, velocity, and/or goodness of fit.

In a specific example, a disclosed method for displaying blood replenishment time in a tissue includes determining a respective initial video intensity for each respective pixel of a plurality of pixels of an ultrasound image taken at or near an initial timepoint at which microbubble contrast agents (that were intravenously introduced prior to the initial timepoint) are destroyed. The respective initial video intensity for each respective pixel is proportional to the concentration of microbubbles in the blood volume within the tissue in a respective location of the tissue corresponding to the respective pixel at the initial timepoint. Methods also may include determining a respective subsequent video intensity of each respective pixel of the plurality of pixels at each of a plurality of subsequent timepoints using a plurality of subsequent ultrasound images taken at the plurality of subsequent timepoints after the initial timepoint to create a dataset. The dataset then may be used to determine a respective steady-state concentration of microbubbles in the blood volume, a respective blood velocity, and a respective time-to-target-replenishment or other parameter value for each respective pixel of the plurality of pixels. The time-to-target-replenishment is the amount of time it takes for the respective subsequent video intensity of each respective pixel to increase from the respective initial video intensity to a predetermined percentage of a respective steady-state video intensity corresponding to the respective steady-state concentration of microbubbles in the blood volume.

Methods also include color-coding the time-to-target-replenishment or other parameter value for each respective pixel using a colormap, wherein the colormap assigns a first color to respective times-to-target-replenishment that are below a predetermined threshold time, and the colormap assigns a second color to respective times-to-target-replenishment that are above the predetermined threshold time. The first color is different from the second color, and generally is configured to provide a contrast between one another, to easily distinguish between color-coded pixels and areas of color-coded pixels in a resulting output image. To this end, methods also include creating and displaying such an output image that displays the plurality of pixels, wherein the plurality of pixels are color-coded according to the color assigned to each pixel based on its respective time-to-target-replenishment. Disclosed methods thereby are configured to differentiate between one or more portions of the tissue experiencing respective times-to-target-replenishment that are below the predetermined threshold time value and one or more portions of the tissue experiencing respective times-to-target-replenishment that are above the predetermined threshold time value.

Systems for processing blood replenishment time in a tissue also are within the scope of the present disclosure and may include an ultrasonic transducer probe configured to send and receive ultrasonic waves via a tissue by converting electrical energy into acoustic pulses and vice versa, a pulse transmitter configured to generate pulsed echo signals in brief bursts, a controller configured to control a transducer-pulse emitted from the ultrasonic transducer probe, a display configured to display one or more images from ultrasound data received from the ultrasonic transducer probe and processed by the processing unit, at least one processing unit operatively coupled to the ultrasonic transducer probe and responsive to temporal sequences of contrast echo signals from a plurality of respective locations in the tissue, and a memory configured for storing non-transitory computer-readable instructions that, when executed by the at least one processing unit, cause the system to perform methods for displaying blood replenishment time in a tissue, such as those described herein. Computer-readable medium configured for processing and displaying blood replenishment time in a tissue are also within the scope of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION

Figure 1:
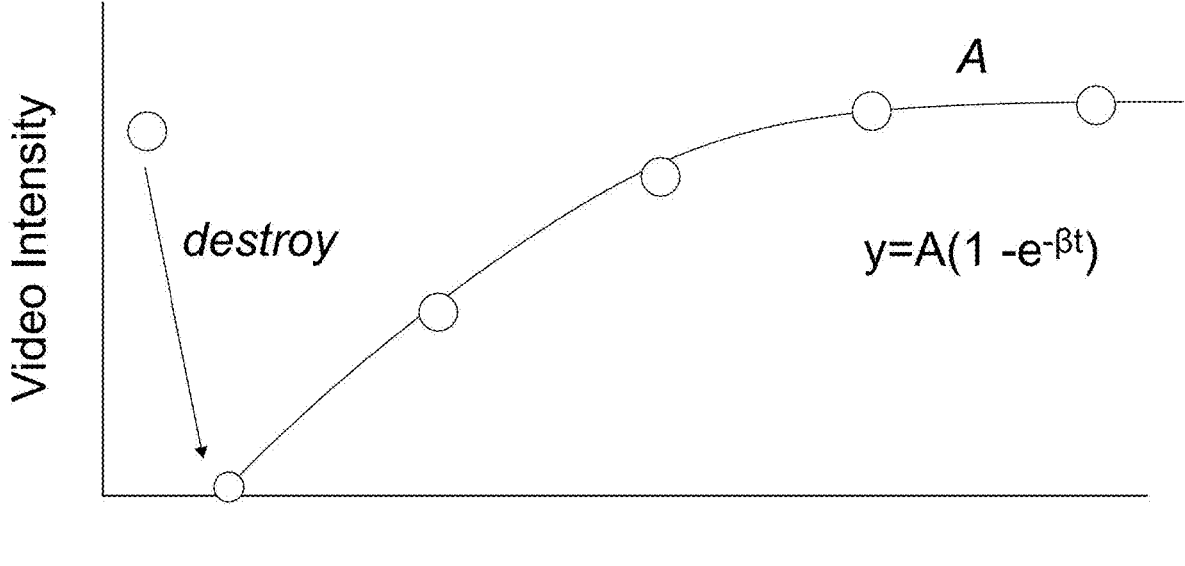
FIG. 1 is a line graph illustrating an example of an exponential curve, modeling replenishment of blood in a tissue.

Microbubble contrast agents, which may also be referred to herein simply as microbubbles, may be injected intravenously into the circulatory system of a patient in a small bolus or using a continuous infusion. While the microbubbles circulate through the body, ultrasound waves are directed on a tissue of interest (e.g., the myocardium), and a plurality of ultrasound images are taken. When the microbubbles in the blood are within an imaging window captured by an ultrasonic transducer, the microbubbles' cores oscillate due to a high-frequency sonic energy field created by the ultrasonic transducer. An echogenicity (i.e., brightness, or video intensity, of an ultrasound image caused by reflection of the ultrasound waves) of the microbubbles is much greater than that of the native tissue, and thus creates a contrast between the microbubbles and the native tissue in the resulting ultrasound image(s) created by an ultrasound system. In this manner, clinicians, researchers, technicians, and other practitioners are able to distinguish microbubble-containing blood from surrounding native tissues. The concentration of the microbubbles in the blood at a given location may be quantified by the video intensity of the pixel(s) at that location.

To model blood replenishment within a tissue or region of interest, the microbubbles are destroyed at a certain time, by applying one or more pulses (typically 5-10) of high-energy ultrasound energy, resulting in rupturing a shell or wall encapsulating the microbubble core. Some or all of the microbubble contrast agents within an area of interest in the tissue may be destroyed as a result of the pulse, though generally a high enough percentage will be destroyed to distinguish subsequently perfusing blood containing non-destroyed microbubbles. For example, a high mechanical index (MI)-pulse may be transmitted via the ultrasonic transducer to destroy substantially all, or at least a majority of, the microbubbles within a thickness or a slab of the area of interest. After the high MI-pulse that destroys the microbubbles within the blood within the tissue, blood cycles through the tissue and, thereby, fresh blood containing non-destroyed microbubbles re-enters (e.g., perfuses) the tissue. The concentration of microbubbles will increase until it reaches a steady-state concentration within the volume of blood of the tissue. Ultrasound images are taken as the blood cycles through an area of interest to observe and quantify new non-destroyed microbubbles re-entering the tissue. The faster the blood flows through the body's vasculature and microvasculature, the quicker the new non-destroyed microbubbles will reappear in the tissue after the initial destruction. The ultrasound images are recorded and image-processed to create time-video intensity curves representing the replenishment rate of blood into the tissue. In some examples electrocardiogram (ECG) signals also may be recorded simultaneously with the ultrasound images and used in the data analysis as well.

Thus, according to the present disclosure, the replenishment of blood in the myocardium or other tissue over time (t) can be modeled using the brightness, or video intensity, of pixels in a plurality of ultrasound images of the tissue of interest. Such methods may be used to display blood replenishment data for specific locations within the tissue using non-invasive methods, with capabilities of displaying the data in real-time or close to real-time in some examples. Tissues, or certain areas of the tissue, may take different amounts of time to replenish blood when a patient or subject is under physiologic stress, or when portions of the tissue are damaged or diseased. Thus, the blood replenishment time can provide valuable diagnostic information to clinicians, researchers, and practitioners and/or can inform treatment of the patient. While examples herein are largely described with respect to determining the time for blood replenishment of the myocardium, described methods may be applied to other tissues or organs, such as kidneys, liver, skeletal muscle (e.g., calf muscle), uterus, eyes, skin, and/or brain.

In the following equation, A is a constant that represents the steady-state concentration of microbubbles in the blood volume within a particular location of the tissue corresponding to a respective pixel or groups of pixels in an ultrasound image of the tissue, β represents the blood velocity, or blood replenishment rate of that location of the tissue, and y is a measured variable determined by the video intensity of the respective pixel or group of pixels at time t (corresponding to the concentration of microbubbles in that blood volume in the particular location of the tissue at time t):

$$y = A\left(1 - e^{-\beta t}\right)$$

FIG. 1 illustrates an example graph plotting blood replenishment over time for a particular location within a tissue, such as a particular location within the myocardium. In FIG. 1, the y-axis (video intensity) represents the brightness recorded by the ultrasound system at the specific location of the ultrasound image, and corresponds to the concentration of microbubbles in the blood volume at that location, for each time t. Again, after microbubble contrast agents have been introduced into the bloodstream, the microbubbles in the tissue are destroyed at time t=0, and thus the video intensity (y value) is zero or near zero at or just after that time, because blood does not reflect the ultrasound waves without the microbubble contrast agents. As fresh blood perfuses back into the myocardium over time, the blood carries with it non-destroyed microbubbles from the bloodstream, which result in an increasing video intensity over time, as shown in the example exponential curve of FIG. 1. In the time interval after microbubble destruction, the concentration of microbubbles in the sampling volume of the tissue keeps increasing until a plateau is reached, which corresponds to the steady-state microbubble concentration in that blood volume, A. At that moment, at least substantially all blood in the volume where microbubbles were destroyed beforehand by high energy pulses has been replaced by fresh blood that brought in new microbubbles as it perfused into the tissue. The constants A and B are fit simultaneously using the Levenburg-Marquadt algorithm (which statistically optimizes the model to fit the data). As the curve plateaus, y is substantially equal to A, representing a full cycling of blood volume through the tissue. Time t is generally measured starting from the time at which the microbubble contrast agents are destroyed, thus t=1 second would be one second after microbubble destruction, t=2 seconds would be two seconds after microbubble destruction, and so on.

Figures 2A, 2B, 2C, 2D, 2E:
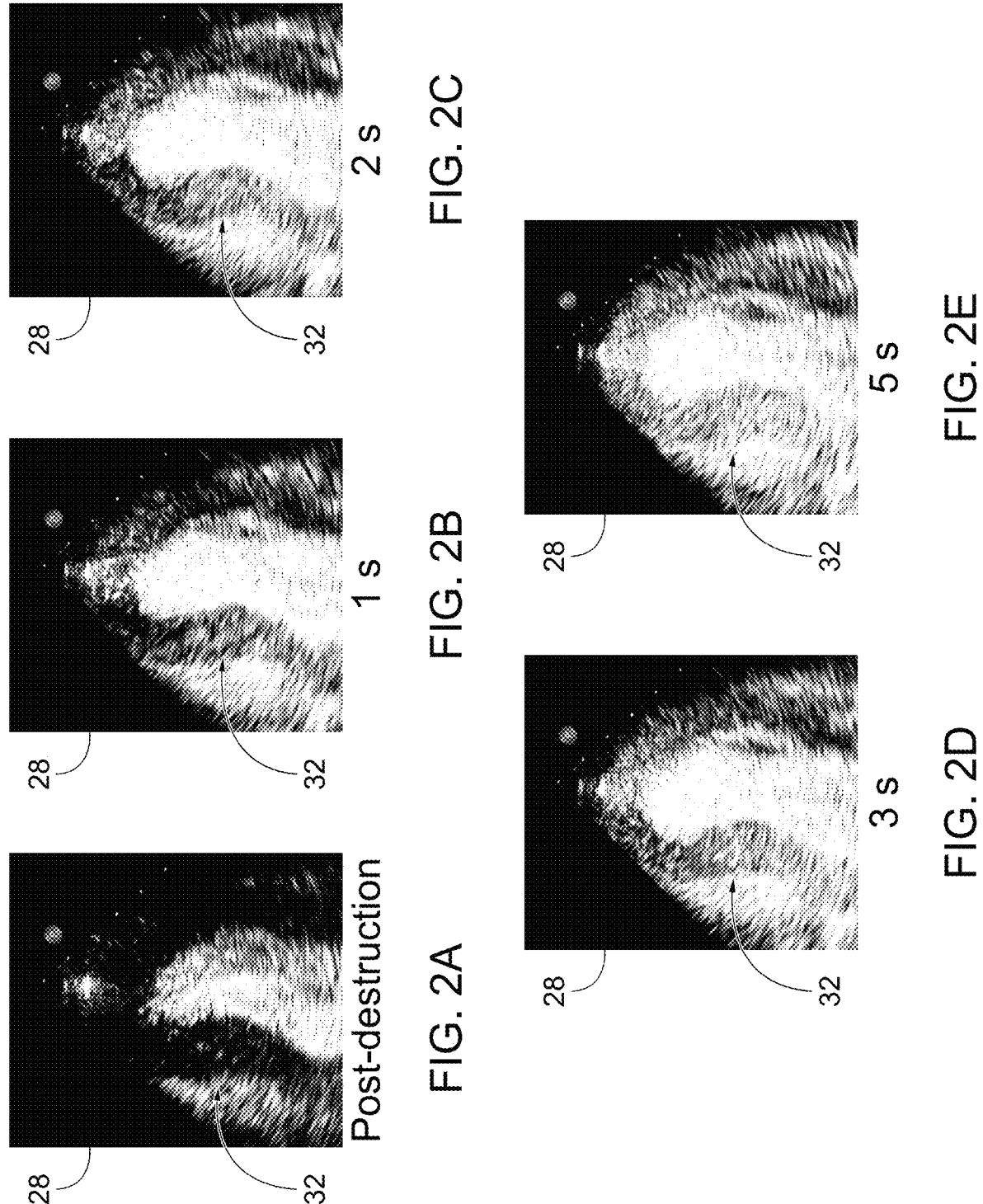
FIGS. 2A-2E are examples of ultrasound images of a myocardial tissue taken at five different timepoints.

Such graphs as that shown in FIG. 1 may be produced for a region of interest within the tissue, with a value calculated using all pixels in the region of interest, and then curve fitting of the data may be performed. The region of interest may be as small as a single pixel, or may cover a significant percentage of the tissue. FIGS. 2A-2E show an example of reference ultrasound images 28 of the myocardium 32, where FIG. 2A shows the ultrasound image (e.g., sonogram) as it appears right after destruction of the microbubble contrast agents, with most of the myocardium 32 appearing black (corresponding to a low or zero video intensity due to lack of microbubbles present after destruction). Generally, an initial ultrasound image, such as that shown in FIG. 2A, will be taken at or near (e.g., as temporally close as possible to) an initial timepoint at which the microbubbles are destroyed (e.g., t=0). The initial video intensity for each respective pixel of a plurality of pixels of the initial ultrasound image is recorded, and a plurality of subsequent ultrasound images 28 are taken at a plurality of subsequent timepoints after microbubble destruction. In some examples, the subsequent timepoints may be selected at the patient's end systole, using a simultaneously recorded ECG signal to determine each end systole. In some examples, the subsequent timepoints may additionally or alternatively be selected at another phase of the heart cycle (e.g., end diastole), and/or based merely on time or other factors.

For example, FIG. 2B shows the ultrasound image of the same area at a time of 1 second after microbubble destruction, FIG. 2C shows the ultrasound image of the same area at 2 seconds after microbubble destruction, FIG. 2D shows the ultrasound image of the same area at 3 seconds after microbubble destruction, and FIG. 2E shows the ultrasound image of the same area at 5 seconds after microbubble destruction. The time of 1 second between each subsequent timepoint is a non-exclusive example, and may correspond to a patient exhibiting a heart rate of 60 beats per minute, though other examples of time between subsequent timepoints also are within the scope of the present disclosure and need not necessarily correspond to the patient's heart rate. The myocardium 32 appears brighter (having an increased video intensity) as time goes on after microbubble destruction, resulting from re-introduction of non-destroyed microbubbles into the myocardium as fresh blood perfuses into the tissue. The brightness of the area increases in proportion to the amount of non-destroyed microbubbles present in the tissue, carried there by perfusion of fresh blood into the tissue. In ultrasound imaging, the strengths of ultrasound echoes that are reflected back are based on the acoustic properties of the tissues or microbubbles. Stronger signals are coded brighter, and weaker signals are coded darker. Thus, the video intensity of the ultrasound image at a given time after destruction of the microbubbles (at t=0), corresponds to the fraction or percentage of the blood volume within the tissue that has been replenished by fresh blood at the respective time the next ultrasound image is taken. Video intensity at time t=0 is subtracted out from other measured video intensities, and the data is curve-fit, as in the example plot shown in FIG. 1.

While conventional techniques have displayed parameters such as the concentration of microbubbles in the blood volume, and/or blood velocity β values as a visual map on the myocardium, practitioners may find these parameters difficult to interpret, and thus conventional methods have been met with limited acceptance in clinical use. Presently disclosed methods and systems utilize the data from myocardial contrast echocardiography (MCE) and process and display the data in ways that are more meaningful to practitioners and easier to interpret. According to the present disclosure, the video intensity of each pixel of an ultrasound image of the myocardium (or other tissue) is measured over time, before, during, and/or after destruction of the microbubble contrast agents. Once the steady-state concentration of microbubbles in the blood volume has been determined (described herein, below), the video intensity associated with that steady-state concentration is known (i.e., the constant, A). The time interval it takes for each pixel to reach a video intensity that is a predetermined percentage of A (e.g., 80% of A) is calculated according to the following equation, where $t_{80}$ for each pixel is the respective amount of time it takes for the respective pixel to reach 80% of the steady-state concentration of microbubbles in the blood volume for that pixel:

$$t_{80} = \frac{1.609}{\beta}$$

Figures 3A, 3B, 3C, 3D:
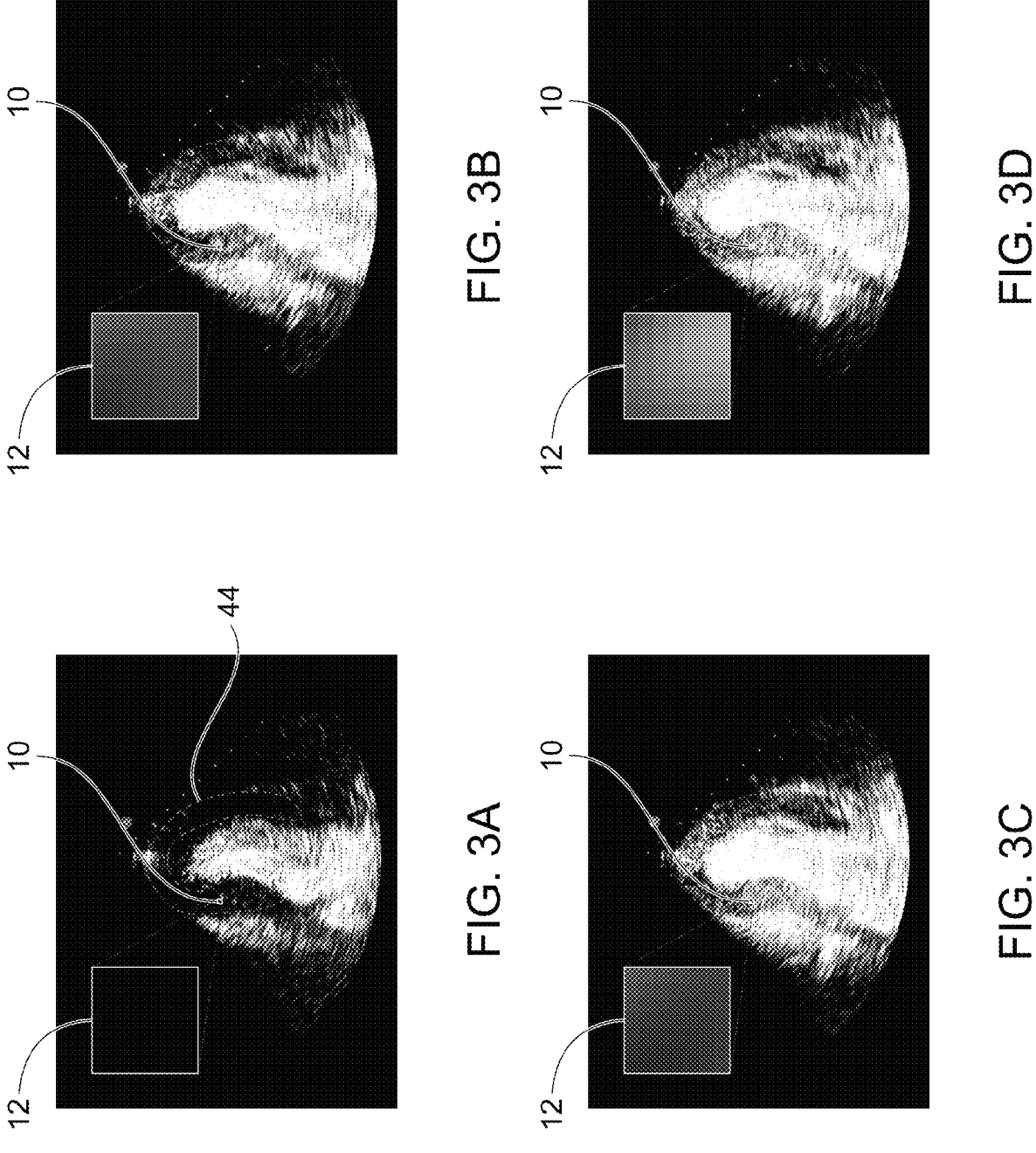
FIGS. 3A-3G are examples of ultrasound images of a myocardial tissue taken at seven different timepoints, illustrating a change in brightness of a respective pixel over time, and surrounding pixel grid around a respective pixel at each respective timepoint.

In order to calculate the value of $t_{80}$ (or the value for another predetermined percentage of A), the ultrasound image is cropped to a grid of pixels that centers on each respective pixel corresponding to the tissue of interest (e.g., the myocardium) in the ultrasound image. In some examples, a 7×7 pixel grid is used, though in other examples a smaller or larger pixel grid may be used. For example, other examples may include cropping the ultrasound image to a 3×3 pixel grid, a 5×5 pixel grid, a 9×9 pixel grid, or an 11×11 pixel grid, with the pixel of interest centered within the grid. In an illustrative example using a 7×7 pixel grid, for each pixel at each time, forty-nine video intensities are input into the curve fitting algorithm. In this manner, the resulting data is then fit to the exponential model (an example of which is shown in FIG. 1) using the Levenberg-Marquardt algorithm to determine the steady-state concentration of microbubbles in the blood volume (A) and blood replenishment rate (B) for each pixel. For example, FIGS. 3A-3G show sequential end-systolic ultrasound images of the myocardium. For each respective pixel of each sequential ultrasound image in FIGS. 3A-3G, the following steps would be performed, though for illustrative purposes, the example of a single respective pixel 10 is herein described. Pixel 10 is visible in the ultrasound image at time t=0 in FIG. 3A. FIG. 4A shows pixel 10 at the center of a 7×7 pixel grid 12 that includes pixel 10 and surrounding pixels 14. These steps are then repeated for each subsequent ultrasound image shown in FIGS. 3B-3G to find corresponding values of y for pixel 10 at the respective times for each respective subsequent ultrasound image in FIGS. 3B-3G. FIGS. 3A-3G illustrate respective surrounding pixel grids 12 for pixel 10, with the pixel grids shown in callouts next to the ultrasound image. While FIGS. 3A-3G show seven sequential ultrasound images for illustrative purposes, disclosed methods may include performing the processing and analysis steps for more or fewer sequential ultrasound images.

Figures 3E, 3F, 3G:
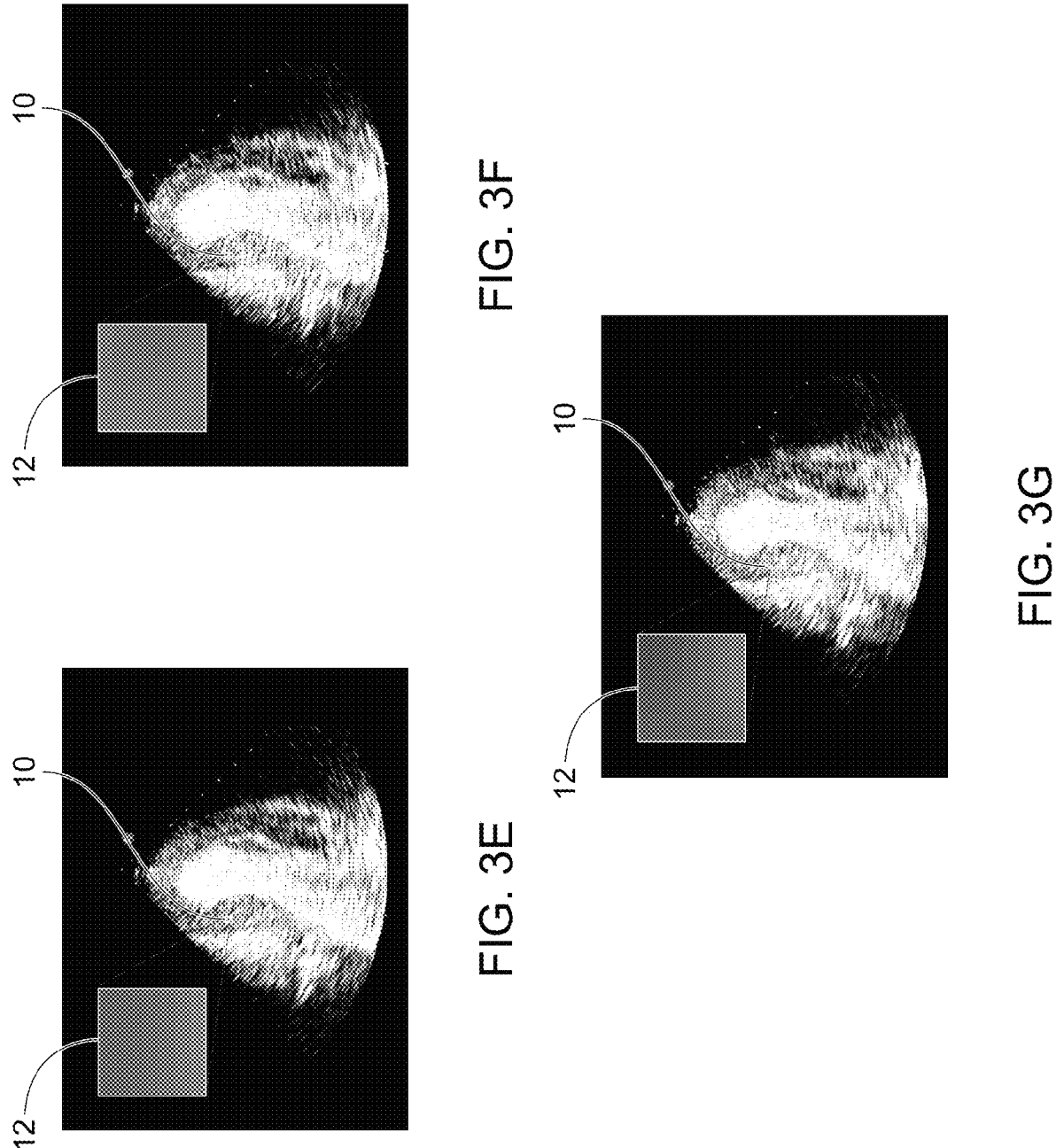
Figures 4A, 4B, 4C, 4D, 4E, 4F, 4G:
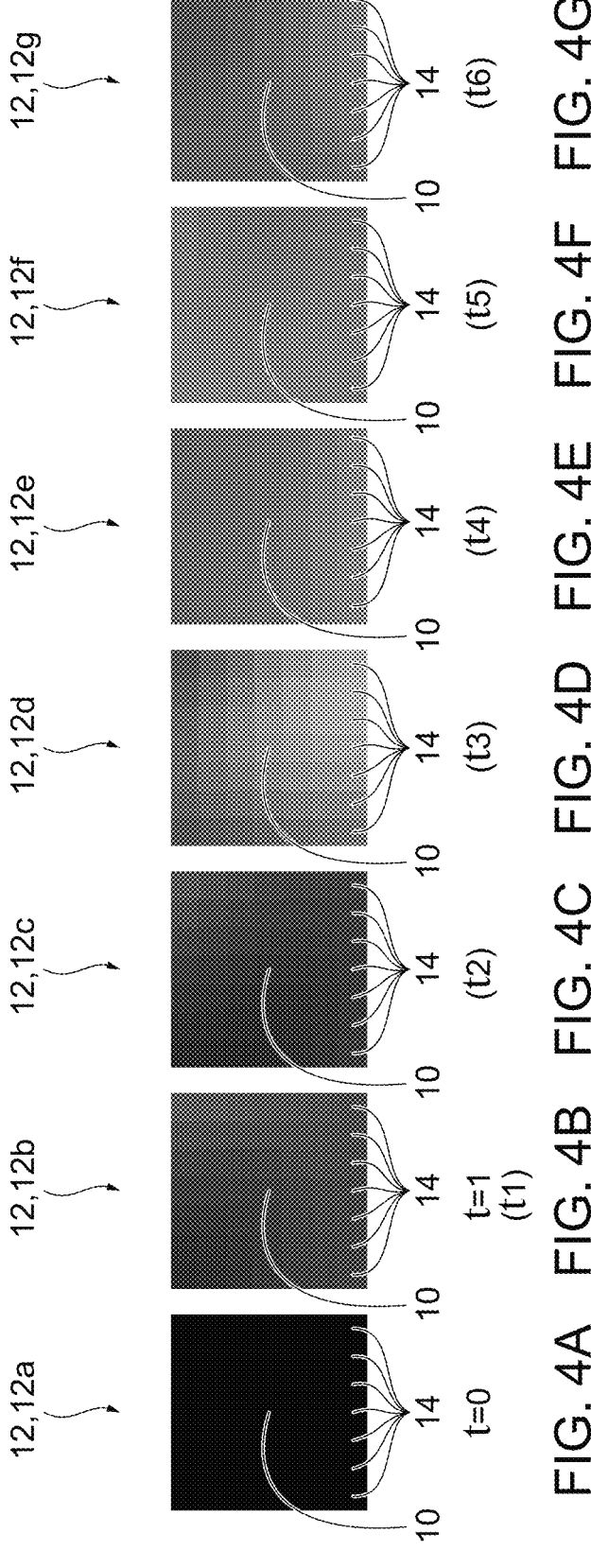
FIGS. 4A-4G show a larger view of the pixel grids from examples of ultrasound images of FIGS. 3A-3G.

FIG. 4B illustrates a close-up of an example of pixel grid 12 that may surround pixel 10 at time t1 (corresponding to the ultrasound image of FIG. 3B), FIG. 4C illustrates an example of pixel grid 12 for pixel 10 at time t2 (corresponding to the ultrasound image of FIG. 3C), FIG. 4D illustrates an example of pixel grid 12 for pixel 10 at time t3 (corresponding to the ultrasound image of FIG. 3D), FIG. 4E illustrates an example of pixel grid 12 for pixel 10 at time t4 (corresponding to the ultrasound image of FIG. 3E), FIG. 4F illustrates an example of pixel grid 12 for pixel 10 at time t5 (corresponding to the ultrasound image of FIG. 3F), and FIG. 4G illustrates an example of pixel grid 12 for pixel 10 at time t6 (corresponding to the ultrasound image of FIG. 3G). Time t1 is after t=0, time t2 is after time t1, and so on. Times t1, t2, t3, and so on may also be referred to herein as timepoints. The elapsed time between each subsequent timepoint t1, t2, t3, and so on may be selected based on criteria for the particular tissue or application being studied, and/or on the patient's heart rate. In some examples, there may be about 0.25 seconds, about 0.5 seconds, about 1 second, about 1.5 seconds, about 2 seconds, or about 2.5 seconds between each subsequent timepoint. In some examples, the time between subsequent timepoints may vary from one timepoint to the next. In some examples, the time between subsequent ultrasound images may be about 60 sec/heart rate (in beats per minute, bpm), or about 1 second for a heart rate of 60 bpm and about 0.667 seconds for a heart rate of 90 bpm. The video intensity across all pixels 10, 14 of each respective pixel grid 12a-g are determined for pixel 10 for each ultrasound image in such sample. These steps are then repeated for each respective pixel of the ultrasound images in such sample, and the data are fit to the exponential equation shown above.

Figure 5:
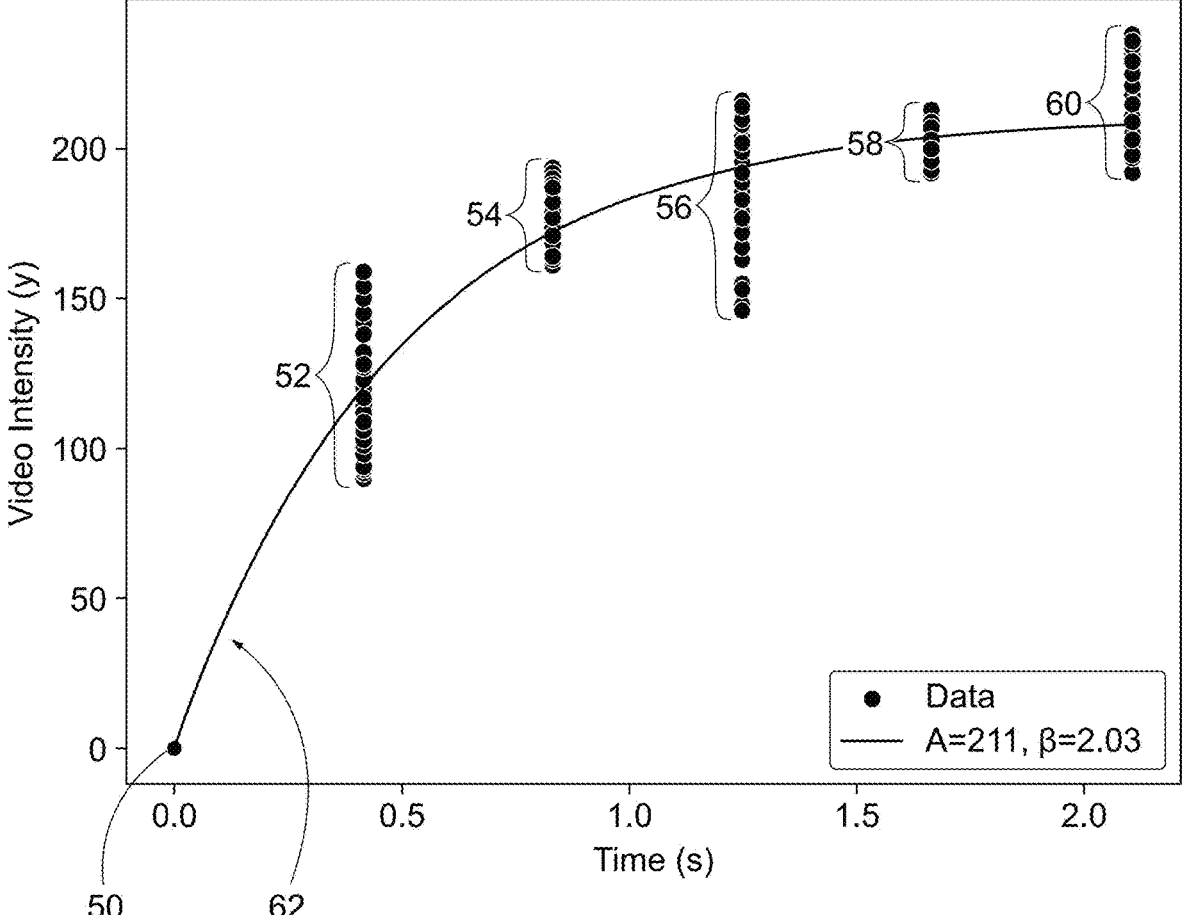
FIG. 5 is a plot graph illustrating an example of video intensity of individual pixels from a pixel grid surrounding a respective pixel, taken at six different timepoints, along with a curve to which the data is fit to determine blood velocity and a steady-state concentration of microbubbles in the blood volume at a respective location of the tissue corresponding to the respective tissue.

To determine the values of the steady-state concentration A of microbubbles in the blood volume and blood replenishment rate β for each pixel in an ultrasound image, the video intensity of each pixel 14 in the respective surrounding pixel grid 12 is plotted at each time for which an ultrasound image is available. For example, at t=0, all of the pixels 14 surrounding pixel 10 have a video intensity of 0 (as shown in pixel grid 12a of FIG. 4A, in which all the pixels 10, 14 are essentially black), which is plotted as point 50 in FIG. 5. At time t1 (which in the example plotted in FIG. 5 is just under 0.5 seconds, but in other examples may be from an ultrasound image taken after more or less elapsed time after microbubble destruction), the pixels 14 of pixel grid 12 (e.g., pixel grid 12b of FIG. 4B) may have a variety of different video intensities, representing a plurality of different rates of blood perfusion into those specific locations of the myocardium. Each measured video intensity for each respective pixel 14 of the pixel grid 12 surrounding pixel 10 from the ultrasound image taken at time t1 is plotted, resulting in a plurality of dots or plot points as indicated at 52 in FIG. 5. As shown in this example, at time t1, the video intensity of pixels 14 of pixel grid 12b range from about 80-160. Similarly, at time t2 (at about 0.8 seconds in the example of FIG. 5), each respective video intensity of each respective pixel 14 of the pixel grid 12 surrounding pixel 10 from the ultrasound image taken at time t2 (e.g., pixel grid 12c of FIG. 4C) is plotted, as indicated at 54 in the example of FIG. 5. In this example, the measured video intensities of pixels 14 from time t2 range from about 150-200, and are more closely clustered than at time t1.

These steps are repeated for each pixel 10, using the respective surrounding pixel grid 12 for each respective pixel 10 at each of the respective times at which the ultrasound images are taken. In FIG. 5, 56 indicates the measured video intensities for each of the forty-nine pixels 14 in pixel grid 12d (FIG. 4D) measured at time t3, 58 indicates the measured video intensities for each of the forty-nine pixels 14 in pixel grid 12e (FIG. 4E) measured at time t4, and 60 indicates the measured video intensities for each of the forty-nine pixels 14 in pixel grid 12f (FIG. 4F) measured at time t5. These video intensities may be plotted as shown in FIG. 5 for each time t for which ultrasound images are available, and then used to determine the steady-state microbubble concentration of the blood volume (A) and blood replenishment rate for each respective pixel 10. Curve 62 shown in FIG. 5 represents the single exponential model that may be computed to fit A and β in the equation for all such timepoints:

$$y = A(1 - e^{-\beta t})$$

All the data points shown in FIG. 5 may be input directly into curve fitting, without any averaging prior to curve fitting. One respective value of steady-state concentration of microbubbles in the blood volume A and one respective value of blood velocity β may be computed for each respective pixel, which models all of the data for a respective single pixel 10. In an illustrative example, the respective steady-state concentration of microbubbles in the blood volume (A) for a respective pixel is determined to correspond to a video intensity 211, and the respective blood replenishment rate β for the respective pixel is determined to be 2.03. The same steps may be performed for each respective pixel 10 of the myocardium, such that a respective steady-state concentration of microbubbles in the blood volume A and blood replenishment rate β may be determined for each respective pixel 10.

Once the steady-state concentration of microbubbles in the blood volume A and blood replenishment rate β are fitted using the Levenburg-Marquadt algorithm, the amount of time it takes after the microbubble contrast agents are destroyed for y to reach a predetermined percentage (e.g., 80%) of A (e.g., $t_{80}$) may be calculated for each pixel in the ultrasound image, as set forth above. This time interval is referred to herein as the "time-to-target-replenishment," or the time it takes for the respective pixel to reach a predetermined, or target, percentage of full replenishment. The time-to-target-replenishment is one example of a parameter value that may be analyzed, color-coded, and overlaid on an ultrasound image according to the present disclosure. Examples described herein with respect to the parameter value being a time-to-target-replenishment are not limited to this particular example of parameter value, and may be adapted to other types of parameter values as described herein. In examples herein, time-to-target-replenishment is described using 80% as the predetermined or target percentage of A, though any desired predetermined percentage may be substituted within the scope of the present disclosure. As other illustrative examples, time-to-target-replenishment may be calculated based on y reaching other predetermined percentages of A, such as 10% of A (denoted below as $t_{10}$), 50% of A (denoted below as $t_{50}$), or 90% of A (denoted below as $t_{90}$), though other time-to-target-replenishment for different predetermined percentages may be calculated based on the exponential equation set forth above on page 15. Different thresholds may be more suitable for different tissues and/or different parameters to be assessed, and thus the predetermined percentage may be selected based on such factors and the percentage that gives the best separation between areas with acceptable and unacceptable reperfusion. In some examples, a sequence of images can be generated, each for a progressively increasing (or decreasing) predetermined percentage, and displayed either as a series of images side by side, or animated as a movie. For these illustrative examples, the respective time-to-target-replenishment may be calculated as follows:

$$t_{10=\frac{0.105}{\beta}} \quad t_{50=\frac{0.693}{\beta}} \quad t_{90=\frac{2.303}{\beta}}$$

After the time-to-target-replenishment (e.g., $t_{80}$) or other parameter value is calculated for each pixel in the myocardium (or other tissue), a diverging colormap (which may also be referred to as a "divergent colormap") may be applied to the data to highlight a clinically-significant threshold for the time-to-target-replenishment. In the example of time-to-target-replenishment, this threshold is a time value, whereas for other parameter values, the threshold values may be values other than time.

Figures 6, 7, 8:
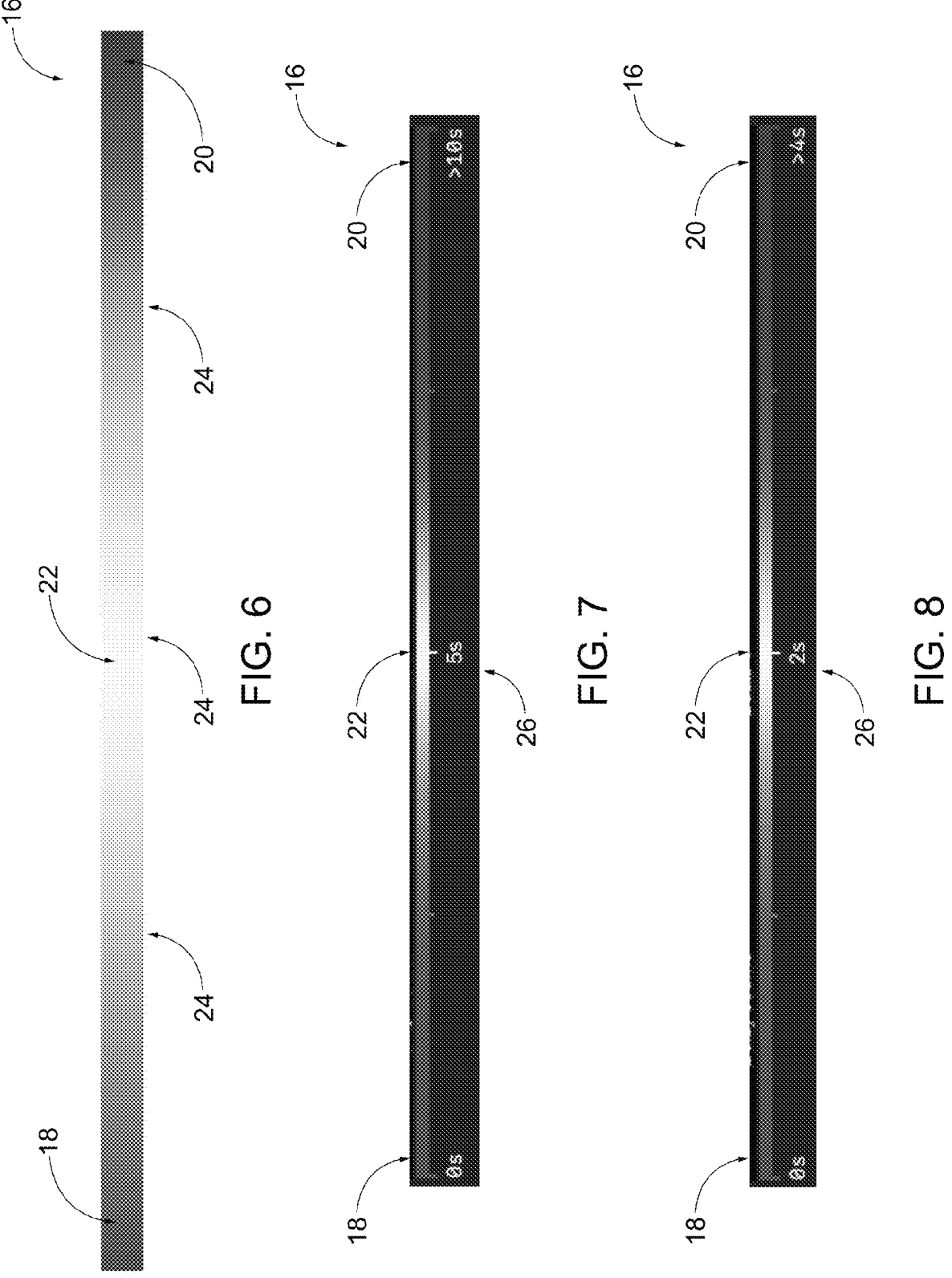
FIG. 6 is an example of a colormap that may be used to color-code blood replenishment time data according to presently disclosed methods and systems.
FIG. 7 is an example of a colormap applied to an example of a time scale that may be used to display blood replenishment time within a tissue by differentiating between areas of the tissue that exhibit blood replenishment times above and below a predetermined threshold blood replenishment time, according to presently disclosed methods and systems.
FIG. 8 is another example of a colormap applied to an example of a time scale that may be used to display blood replenishment time within a tissue by differentiating between areas of the tissue that exhibit blood replenishment times above and below a predetermined threshold blood replenishment time, according to presently disclosed methods and systems.

For example, FIG. 6 illustrates an example of a divergent colormap 16 that may be used in presently disclosed methods. Divergent colormap 16 extends along a gradient 24 from a first color 18 to a second color 20, with a middle region or point 22 being white, substantially white, or a light color that contrasts with first color 18 and second color 20. In disclosed methods, colormap 16 is used to color-code time values, in which first color 18 represents areas of the tissue where blood replenishment is fastest (e.g., where the time-to-target-replenishment is lowest), and second color 20 represents areas of the tissue where blood replenishment is slowest (e.g., wherein the time-to-target-replenishment is highest). Middle region 22 may correspond to an assigned, or predetermined, threshold time for the time-to-target-replenishment, such that the data may be visually presented via colormap 16 with first color 18 displayed on locations (e.g., pixels) of the myocardium or other tissue where the time-to-target-replenishment is below the predetermined threshold time, and second color 20 displayed on locations (e.g., pixels) of the myocardium or other tissue where the time-to-target-replenishment is above the predetermined threshold time. In this manner, a visual image of the myocardium (or other tissue) may, in a single image, display information to practitioners that otherwise would have required complex interpretation of many different images. By contrast, an output image produced via presently disclosed methods may be configured to highlight areas of the myocardium with adequate blood flow and areas of the myocardium with less than ideal, or inadequate, blood flow.

FIG. 7 illustrates an example of colormap 16 as applied to a timescale 26 where the predetermined threshold time of the time-to-target-replenishment is 5 seconds(s). In studies of myocardial tissue when the patient is at rest, 5 s may be seen as a defining threshold time between generally healthy tissue and generally unhealthy tissue. For example, if a pixel of the imaged myocardium demonstrates blood perfusion such that the blood volume reaches the predetermined percentage of the steady-state concentration of microbubbles in the blood volume in under 5 s after the microbubble destruction, that pixel may be displayed as first color 18, with darker shades of first color 18 displayed for respective pixels reaching a video intensity corresponding to the predetermined percentage of A in the shortest amount of time, and lighter shades of first color 18 may be displayed for respective pixels reaching the predetermined percentage of the steady-state concentration of microbubbles in the blood volume in longer times, that are still lower than the predetermined threshold time. Pixels that reach the predetermined percentage (e.g., 80%, in this example) of the steady-state concentration of microbubbles in the blood volume A in exactly the predetermined threshold time (e.g., in exactly 5 s) after microbubble destruction (or within an allowable range on either side of the predetermined threshold time) are displayed in the lightest color of colormap 16, positioned in middle region 22 (e.g., white in the example of FIG. 7). Pixels that display slower replenishment of blood into those areas of the tissue, where it takes longer than the predetermined threshold time (e.g., longer than 5 s) to reach the predetermined percentage of the steady-state concentration of microbubbles in the blood volume A, are illustrated in second color 20, with darker shades of second color 20 representing the slowest blood replenishment times (e.g., the highest times-to-target-replenishment), and with lighter shades of second color 20 representing blood replenishment times that are slower than the predetermined threshold time, yet not as slow to replenish as pixels represented in the darker shades of second color 20. Put another way, in the example of FIG. 7, pixels that reach the predetermined percentage of the steady-state concentration of microbubbles in the blood volume A in less than 5 s are displayed as green in the output image (with darker shades representing faster blood replenishment times), and pixels that reach the predetermined percentage of the steady-state concentration of microbubbles in the blood volume A in greater than 5 s are displayed as reddish pink/purple (with darker shades representing slower blood replenishment times). Suitable colormaps 16 are not limited to the example colors shown, but are selected to have contrasting first and second colors 18, 20 to facilitate interpretation by researchers and clinicians viewing the output image. In some examples, an alternative color map may be used, which may provide individuals with impaired perception of colors ("colorblindness") who have difficulties to distinguish proportions of reds and greens, the ability to correctly interpret time-to-target-replenishment images.

The predetermined threshold time for this example is 5 s because of its clinical significance to the example at hand; though in other examples, different threshold times may be predetermined for different applications, such as for different types of tissues, different disease states, and/or many other relevant factors that would be apparent to those of ordinary skill in the art. Similarly, while a time range 26 of the example of FIG. 7 ranges from 0 s to 10 s or greater, different time ranges 26 may be applied to colormaps 16 as needed for different applications of methods disclosed herein. Additionally or alternatively, the particular colormap 16 illustrated herein is not limiting, and many suitable colormaps may be used in place of the illustrated example of colormap 16, as discussed herein.

FIG. 8 illustrates another example of colormap 16 as applied to a different timescale 26 ranging from 0 s to 4 s or more, where the predetermined threshold time of the time-to-target-replenishment is 2 s. In studies of myocardial tissue when the patient is under stress (e.g., undergoing physical activity, and/or given a pharmacological agent to simulate exercise), 2s may be seen as a defining threshold time between generally healthy tissue and generally unhealthy tissue for blood to replenish to 80% of the steady-state concentration of microbubbles in the blood volume. Thus, the colormap 16 and time range 26 of the example of FIG. 8 displays an output image according to presently disclosed methods, in which pixels of the myocardium that take longer than 2 s to replenish to the predetermined percentage (e.g., 80%) of the steady-state concentration of microbubbles in the blood volume appear as a shade of pink/purple (with darker shades for longer times-to-target-replenishment), while pixels of the myocardium that take less than 2 s to replenish to the predetermined percentage of the steady-state concentration of microbubbles in the blood volume appear as a shade of green (with darker shades for shorter times-to-target-replenishment).

Figure 9:
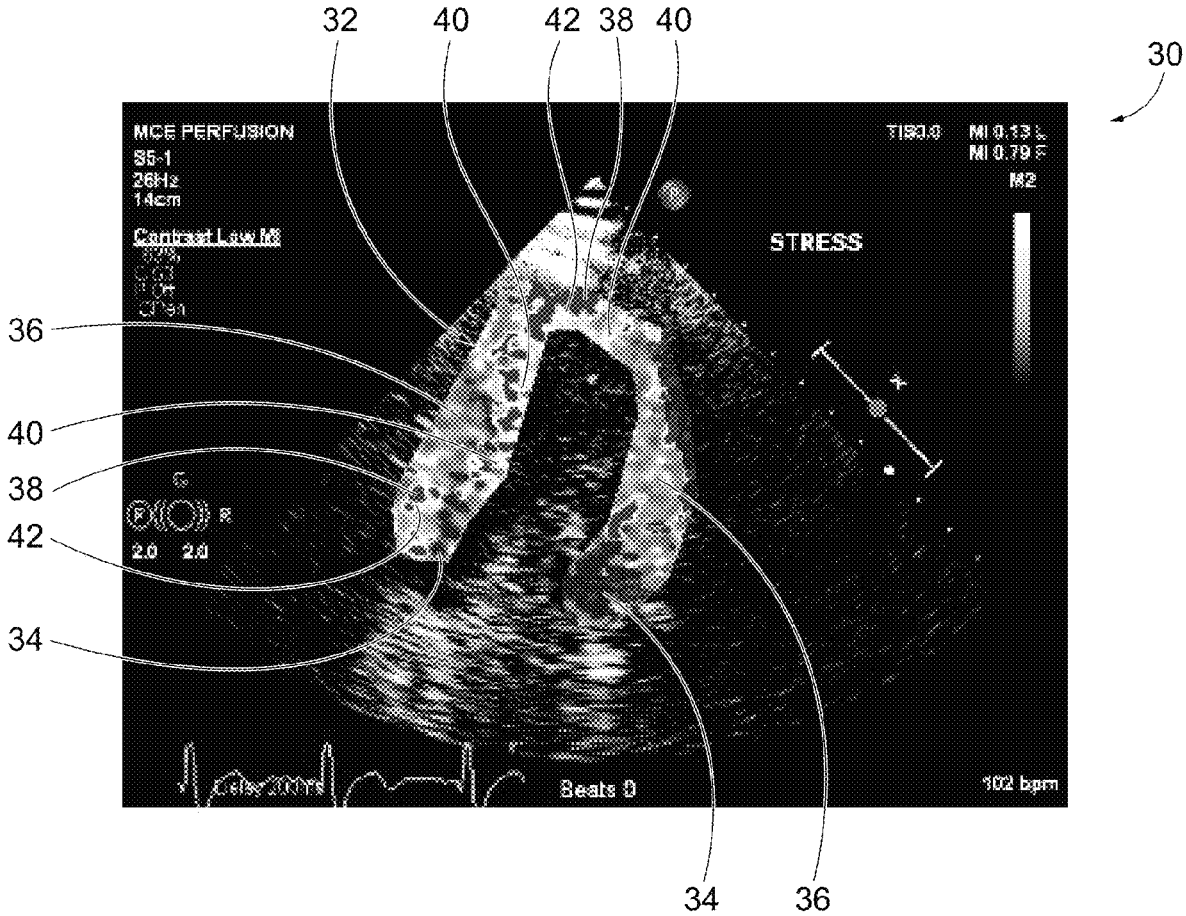
FIG. 9 is an example of an output image generated by presently disclosed systems and methods, where blood replenishment time within a tissue is displayed and areas of the tissue that exhibit blood replenishment times above and below a predetermined threshold blood replenishment time are differentiated from one another.

FIG. 9 illustrates an example of an output image 30 that may be generated, or produced, according to presently disclosed methods. FIG. 9 is an ultrasound image of a patient's myocardium 32, where the visual appearance of the myocardium has been altered from a standard ultrasound output, according to presently disclosed methods. Specifically, each pixel of myocardium 32 is color-coded according to a colormap 16 and a time range 26 (which may be one of the examples of FIG. 7 or 8, or a different colormap 16 and/or a different time range 26), based on the respective time-to-target-replenishment determined for each respective pixel of the ultrasound image of myocardium 32. In this manner, areas of myocardium 32 that are experiencing adequate perfusion of blood (e.g., with a respective time-to-target-replenishment below the predetermined threshold time) may be easily visualized in a single output image 30 by coloring these areas of myocardium 32 a first color 18 (e.g., green in the example of FIG. 9). For example, areas 34 indicate areas of myocardium 32 where the pixels are colored dark green (or other first color 18), thereby indicating areas of healthy tissue (based on calculation of the respective time-to-target-replenishment for each of those respective pixels, as described herein). Areas 36 indicate areas of myocardium 32 where the respective pixels are colored a lighter shade of green (or other first color 18), thereby indicating areas of healthy tissue where the respective time-to-target-replenishment is slightly slower than dark green areas 34, but still faster than the predetermined threshold time for the time-to-target-replenishment (e.g., faster than 2 s in the illustrated example).

Similarly, areas of myocardium 32 that experience less than adequate perfusion of blood (e.g., with time-to-target-replenishment greater than the predetermined threshold time) may be easily visualized in a single output image 30 in which these areas of myocardium 32 are colored a second color 20 (e.g., pink/purple in the example of FIG. 9). In such examples, areas 38 indicate areas of myocardium 32 where the pixels are colored dark purple (or other second color 20), thereby indicating areas of potentially unhealthy tissue (based on calculation of a respective time-to-target-replenishment for each of those pixels, as described herein). Areas 40 indicate areas of myocardium 32 where the pixels are colored a lighter shade of pink/purple (or other second color 20), thereby indicating areas of potentially unhealthy tissue, where the time-to-target-replenishment is slightly faster than dark purple areas 38, but still slower than the predetermined threshold time for the time-to-target-replenishment (e.g., slower than 2 s in the illustrated example).

Areas 38, 40 where the myocardium 32 illustrates respective times-to-target-replenishment that are slower than the predetermined threshold time (e.g., 2 s or 5 s) may indicate areas of some obstruction within the myocardium, which may be used to help indicate diagnosis or determine treatment plans. Areas of myocardium 32 where the time-to-target-replenishment for the respective pixel is equal or substantially equal to the predetermined threshold time are shown in white, or near white coloration, examples of which are indicated at 42 in the example of FIG. 9. White or near white areas 42 may often occur at transition areas between pixels of myocardium 32 that experience blood replenishment faster than the predetermined threshold time (e.g., green areas 34, 36) and pixels of myocardium 32 that experience blood replenishment slower than the predetermined threshold time (e.g., pink/purple areas 38, 40). Such methods and output images 30 allow clinicians, researchers, and practitioners to more easily and quickly recognize characteristic findings indicative of disease conditions, thus aiding in diagnostic evaluation of such data. Other beneficial uses may include: (1) providing easy-to-learn diagnostic images for training fellows and medical students; (2) presenting images in simplified comprehensive displays for side-by-side comparisons in longitudinal studies; and (3) presenting findings to patients and their care teams in a way that improves their understanding of their condition, which has been shown to lead to their higher involvement in care.

In some examples, output image 30 may effectively encode additional information about the data displayed. For example, one or more pixels of output image 30 may be made to appear transparent when one or more model criterion are not met, thereby indicating a lower confidence level in the data displayed. In some examples, these model criteria may include certain threshold values for the determined steady-state concentration of microbubbles in the blood volume, certain threshold values for blood replenishment rate, blood replenishment time, or blood velocity β, and/or a standard error of the fit of the model being greater than a predetermined threshold value. In an illustrative example, pixels of output image 30 may be made to appear transparent if the steady-state concentration of microbubbles in the blood volume is determined to be less than a video intensity of 10, if blood velocity β is determined to be greater than 250, and/or if the standard error of fit of the model is greater than 300. These types of criteria and the application of transparency to the relevant pixels may be utilized to effectively suppress visualization of the relevant pixels of output image 30 when the model is outside of reasonable criteria, though the specific numerical examples of such criteria above are merely for illustrative purposes and are non-limiting. The application of transparency may be said to visually represent "the goodness of fit" of the data. Output image 30 also may be displayed in the context of raw data from the ultrasound procedure. For example, output image 30 may be displayed next to one or more raw ultrasound images used to generate output image 30. Output image 30 may display additional information or data as desired for a given application. In the non-limiting example of FIG. 9, data such as heart rate, ECG signals, an indication as to whether the patient was at rest or under stress, and details regarding the microbubble contrast agent used may be displayed in output image 30, along with the blood replenishment time threshold indication according to the present disclosure.

While examples of predetermined threshold times have been discussed herein (e.g., 2 s and 5 s), predetermined threshold times may be selected that are higher or lower than the examples given herein, such as in cases of analysis of different types of tissues, different patient populations, and/or for different pathologies and phenotypes. Disclosed methods may include determining and/or selecting the predetermined threshold time(s) (or other threshold value for other parameter values) based on factors relevant to the particular application at hand.

Examples described herein focus on the time it takes for a pixel of the myocardium to be replenished to 80% of its steady-state microbubble concentration in the blood volume (e.g., 80% of A) (said time being referred to herein as the time-to-target-replenishment), however, in other examples, other percentages may be more clinically relevant, and therefore used instead. For example, methods described herein may be applied with respect to predetermined percentages that are less than 80% of the steady-state concentration of microbubbles in the blood volume, such as a predetermined percentage that is at least 50% of the steady-state concentration, at least 60% of the steady-state concentration, and/or at least 70% of the steady-state concentration. In other words, rather than determining $t_{80}$ for each pixel in a tissue, methods may include determining $t_{50}$, $t_{60}$, $t_{70}$, and/or a value above, below, and/or in between. In some examples, methods described herein may be applied with respect to greater than 80% of the steady-state concentration of microbubbles in the blood volume, such as a predetermined percentage that is greater than 85% of the steady-state concentration of microbubbles in the blood volume, greater than 90% of the steady-state concentration, and/or greater than 95% of the steady-state concentration.

In a specific example, the PiYG colormap from Matplotlib may be used to visualize the data discussed above (see FIGS. 6-8), though other colormaps also are within the scope of the present disclosure and may be suitable for use as colormap 16. For example, other suitable divergent colormaps may be created using monotonically increasing lightness values up to a maximum lightness value, followed by monotonically decreasing lightness values, with approximately equal minimum lightness values at opposite ends of the colormap. Other divergent colormaps from Matplotlib that may be useful for displaying data discussed herein may include the PRGn, BrBG, PuOr, RdGy, RdBu, RdYlBu, RdYlGn, Spectral, Coolwarm, BWR, and Seismic colormaps. These colormaps create a separation and/or gradient between two colors, such as between pink and green, between purple and orange, or between red and blue. In some examples, other divergent colormaps, or other types of colormaps may be used to represent desired data, such as sequential, cyclic, qualitative, and/or miscellaneous colormaps.

Additionally or alternatively, output image 30 may display other parameter values. For example, as discussed herein, β represents the blood velocity, or blood replenishment rate of that location of the tissue, with β generally being slower when the subject is at rest, and β generally being faster for the same tissue or area of interest when the subject is under physiologic stress. However, certain defects may cause β to not increase under stress or to increase less than would otherwise be expected. To this end, an output image 30 may be created that displays a ratio of β when the subject is under stress, to β when the subject is at rest, which is referred to herein as $\beta_{reserve}$:

$$\beta_{reserve} = \frac{\beta stress}{\beta rest}$$

$\beta_{reserve}$ may then be measured and displayed as a parametric image for each pixel of the myocardium or other tissue. To do so and with reference to FIG. 10, a parametric map of $\beta_{rest}$ may be created with a blood replenishment rate β being measured for each pixel of an ultrasound image 28 of the tissue (e.g., myocardium 32) when the subject is at rest, as described herein. The determined value for blood replenishment rate for each pixel is color-coded and overlaid onto the ultrasound image as shown, to visually represent blood replenishment rate in different areas of the myocardium when the subject is at rest. For example, pixels of the myocardium 32 are color-coded in shades of blue, purple, and grey in FIG. 10, and overlaid onto the ultrasound image 28.

Figure 10:
FIG. 10 is an example of an ultrasound image of a myocardial tissue taken when the subject is at rest, overlaid with a parametric map of blood replenishment time within the myocardial tissue at the time the ultrasound image was taken.
Figure 11:
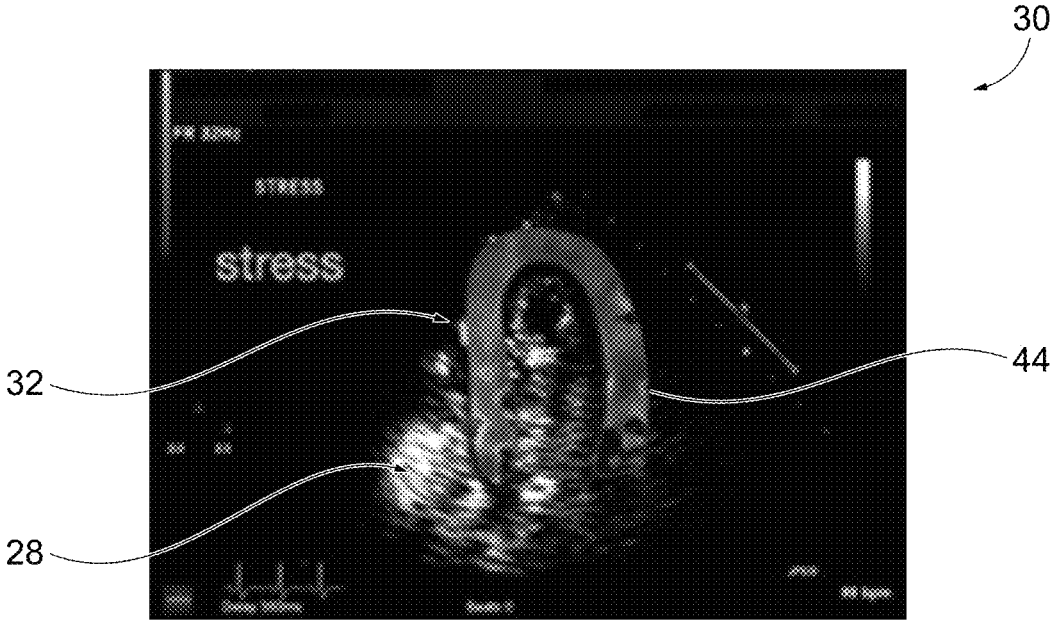
FIG. 11 is an example of an ultrasound image of a myocardial tissue taken when the subject is under physiological stress, overlaid with a parametric map of blood replenishment time within the myocardial tissue at the time the ultrasound image was taken.

Similarly, a parametric map of $\beta_{stress}$ may be created, as shown in FIG. 11, with a blood replenishment rate β being measured for each pixel of an ultrasound image 28 of the tissue when the subject is under stress, as described herein. The determined value for blood replenishment rate for each pixel is color-coded and overlaid onto the ultrasound image 28 to visually represent blood replenishment rate in different areas of the myocardium when the subject is under stress. For example, pixels of the myocardium 32 are color-coded in shades of blue, purple, yellow, and grey in FIG. 11, and overlaid onto the ultrasound image 28. The respective ultrasound scans shown in FIG. 10 and FIG. 11 are taken at different times, as understood in the art. Presently disclosed methods allow for information to be extracted from each of the parametric maps of FIGS. 10 and 11, and displayed as a single output image 30, as shown in FIG. 12, which shows a parametric map of $\beta_{reserve}$ for each pixel of the myocardium 32, overlaid onto a processed ultrasound image 28 of the tissue.

Figure 12:
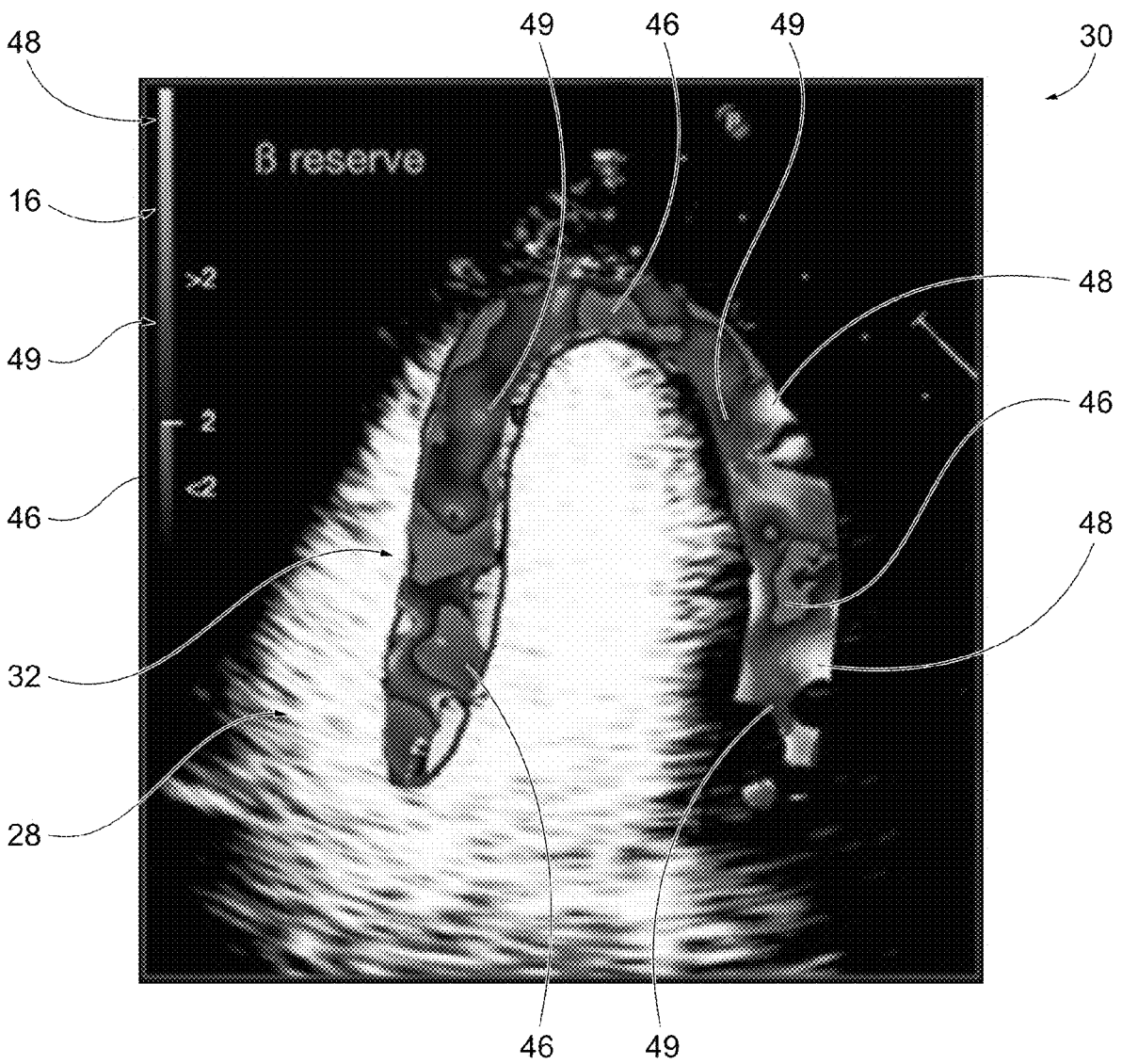
FIG. 12 is a composite parametric image displaying the ratio of blood replenishment time when the subject is under physiological stress to the blood replenishment time when the subject is at rest.

To create the output image 30 shown in FIG. 12, the ultrasound image 28 of the tissue at rest (FIG. 10) may need to be aligned with respect to the ultrasound image 28 of the tissue under stress (FIG. 11), due to changes in shape and position to the myocardium 32 when the tissue is under stress versus at rest and to determine which pixels in one ultrasound image correspond to which pixels in the second ultrasound image. This process may include "segmentation" and/or "registration" and will be understood by those of ordinary skill in the art. Coherent point drift may be used to use the contours generated during segmentation for non-rigid registration of two segmented images. For example, by examining the shape of the myocardial tissue 32 in FIG. 10 and comparing it to the shape of the myocardial tissue 32 in FIG. 11, one can see that the two shapes are slightly different. Briefly, contours or boundaries 44 of the myocardium 32 are outlined both at rest and under stress, which is typically performed manually (see, e.g., FIGS. 3A-3G, dashed line outlines 44 added to show the boundary 44 of the myocardium 32, though best visible in FIG. 3A). Then the boundary 44 of the myocardium 32 under stress (FIG. 11) is modified, such as by being warped, shifted, and/or otherwise modified, to match the contour 44 of the tissue 32 at rest (FIG. 10). To align the images together, a non-rigid transformation may be used to find the position with the minimum amount of error to ensure that as many pixels as possible correspond to the same area of tissue when the images are combined in the output image 30 of FIG. 12. In the output image 30 of FIG. 12, $\beta_{reserve}$ values of less than or equal to 2 (the predetermined threshold value) are represented by shades of gray 46, and $\beta_{reserve}$ values of greater than 2 are represented by the magma color palette (an example of colormap 16). In this example, the areas of myocardium 32 with the highest $\beta_{reserve}$ values are shown in shades of yellow 48 overlaid onto the ultrasound image 28, while areas of myocardium 32 with $\beta_{reserve}$ values above the threshold value but lower than the highest values are shown in magenta, purple, and blue 49. The threshold value of $\beta_{reserve}$=2.0 is selected because it is clinically considered the threshold value between normal $\beta_{reserve}$ (>2) and abnormal $\beta_{reserve}$ (<=2), though other threshold values also are within the scope of the present disclosure.

Because measurements of blood replenishment rate β and concentration of microbubbles in the blood volume A in tissues are relative and not absolute with such methods, metrics may be chosen and displayed that are less influenced by system settings or a particular patient or subject being imaged. In some examples, A fluctuates more than B, and thus the present disclosure describes $\beta_{reserve}$, though creating similar output images using different metrics, such as those of A, $A_{reserve}$, A*β, and/or A*$\beta_{reserve}$ is also within the scope of the present disclosure. As described herein, creating a parametric image of $\beta_{reserve}$ as shown in FIG. 12 may be configured to provide a sensitive, quantitative indicator of compromised myocardial perfusion.

Figure 13:
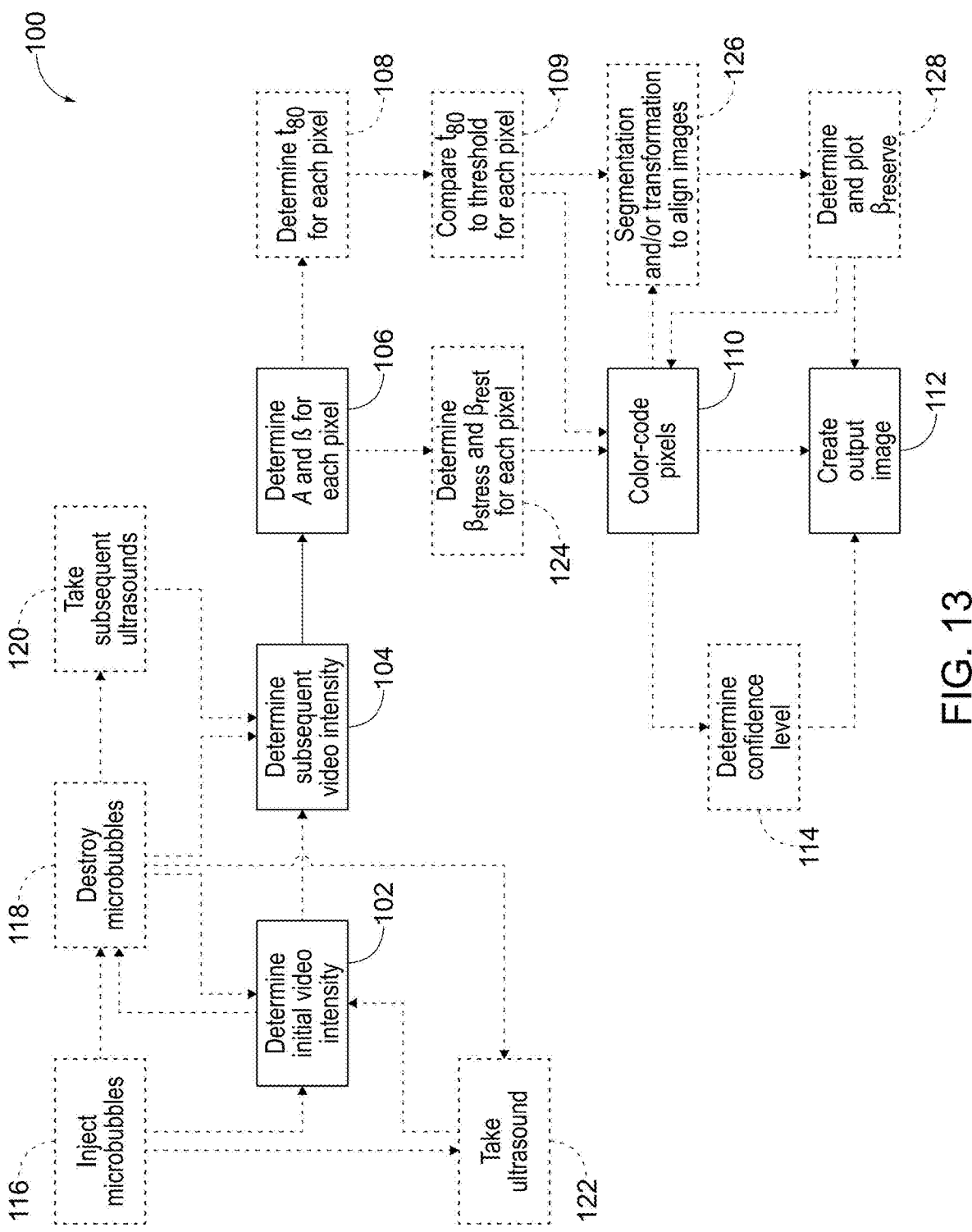
FIG. 13 is a schematic flowchart representation of illustrative, non-exclusive examples of methods for displaying blood replenishment time in a tissue, according to the present disclosure.

FIG. 13 schematically provides a flowchart that represents illustrative, non-exclusive examples of methods 100 for effectively displaying blood replenishment time in a tissue, according to the present disclosure. In FIG. 13, some steps are illustrated in dashed-line boxes, indicating that such steps may be optional or may correspond to an optional version of a method according to the present disclosure. That said, not all methods 100 according to the present disclosure are required to include the steps illustrated in solid line boxes. The methods 100 and steps illustrated in FIG. 13 are not limiting, and other methods and steps are within the scope of the present disclosure, including methods having greater than or fewer than the number of steps illustrated, as understood from the discussions herein.

Methods 100 generally include determining an initial video intensity for each respective pixel in a region of interest (e.g., a tissue, such as the myocardium or a portion thereof) at 102, determining a plurality of subsequent video intensities for each respective pixel at 104, and using the data determined from steps 102 and 104 to determine a steady-state concentration of microbubbles in the relevant blood volume and a blood velocity for each respective pixel at 106. Then, methods 100 also may include determining a time-to-target-replenishment (or other parameter value) for each respective pixel at 108 based on the determined steady-state concentration of microbubbles and blood velocity. Once the time-to-target-replenishment is determined for each respective pixel at 108, methods 100 include color-coding the pixels at 110 to differentiate between pixels that have a time-to-target-replenishment above a predetermined threshold time (or other parameter value) or below the predetermined threshold time or other parameter value. Additionally or alternatively, methods 100 may include determining the blood replenishment time for each pixel both at rest and under stress, at 124. The pixels may then be color-coded at 110 to differentiate between pixels that have a blood replenishment time above and below a predetermined threshold value, with the threshold values generally being different for the at rest and under stress conditions.

Then, an output image (e.g., output image 30) is created and displayed at 112, showing the color-coded pixels overlaid on an ultrasound image of a region of interest, to visualize in one image the areas of the region of interest having, for example, adequate blood replenishment times or times-to-target-replenishment, contrasted with the areas of the region of interest having inadequate blood replenishment rates or too slow of times-to-target-replenishment. The use of a simple predetermined threshold time for evaluating the respective time-to-target-replenishment allows for complex data to be displayed in a relatively easy-to-understand and quick-to-interpret way as compared to prior art techniques, thereby making it more practically useful in clinical and research settings. Additionally or alternatively, an output image showing the resulting parametric images for the at rest condition and the under stress condition may be overlaid onto the corresponding respective ultrasound images to create a respective output image at 112 for the at rest condition and the under stress condition. Some or all of methods 100 may be computer-implemented and/or automated, with human input to set predetermined thresholds, target percentage for time-to-target-replenishment, and number of surrounding pixels to use in the pixel grid.

In some examples, the output images may be segmented and/or transformed to align the images together at 126, such as may be performed for a first output image, showing blood replenishment rate at rest and a second output image, showing blood replenishment rate under stress. Once these values have been determined for each pixel of the tissue of interest, other metrics or values may be determined and mapped at 128, such as $\beta_{reserve}$, as described herein. An additional output image may then be created and displayed at 112, which maps color-coded pixels representing $\beta_{reserve}$ that are overlaid onto an ultrasound image of the tissue.

Determining the initial video intensity of each pixel at 102 may be performed using an ultrasound image taken at or near an initial timepoint at which microbubble contrast agents are destroyed within the tissue, such as at timepoint to of the ultrasound image shown in FIG. 3A. The respective initial video intensity for each respective pixel is proportional to a concentration of microbubbles in the blood volume within a respective location of the region of interest corresponding to the respective pixel at the initial timepoint. Determining the respective subsequent video intensity of each respective pixel at each of a plurality of subsequent timepoints at 104 may be performed using a plurality of subsequent ultrasound images taken at the plurality of subsequent timepoints after the initial timepoint to create a dataset. For example, said determining the subsequent video intensities at 104 may be performed for each pixel in each of the ultrasound images shown in FIGS. 3B-3G. The dataset may be curve-fit to a model (e.g., the equation on page 10 herein) to determine the respective steady-state microbubble concentration in the blood volume and the blood velocity for each respective pixel of the region of interest at 106. Methods 100 also may include calculating the time-to-target-replenishment at 108 for each pixel, using the equation on page 12. As discussed herein, the time-to-target-replenishment is the amount of time it takes for the respective subsequent video intensity of each respective pixel to increase from the respective initial video intensity (measured at 102) to a predetermined percentage (e.g., a target percentage) of a respective video intensity corresponding to the respective steady-state concentration of microbubbles in the blood volume (determined at 106). While the predetermined percentage may be 80% in some examples, in other methods 100, other percentages that are lower or higher than 80% may be used as desired.

Subsequent to the calculating the time-to-target-replenishment at 108 for each pixel in the ultrasound image of the tissue being studied, methods 100 include comparing the time-to-target-replenishment for each pixel at 109 to a predetermined threshold time to determine whether the time-to-target-replenishment for the respective pixel is higher than (e.g., slower than) the predetermined threshold time or lower than (e.g., faster than) the predetermined threshold time. Comparing the time-to-target-replenishment of each respective pixel to the predetermined threshold time at 109 may include selecting the predetermined threshold time. Subsequently, each respective pixel is color-coded at 110 based on the result of the comparison at 109. Specifically, color-coding the time-to-target-replenishment for each respective pixel of the plurality of pixels at 110 may include selecting and using a colormap (e.g., diverging colormap 16 of FIG. 7) to assign a first color to respective pixels having respective time-to-target-replenishment values that are faster than the predetermined threshold time, and to assign a second color to respective pixels having respective time-to-target-replenishment values that are slower than the predetermined threshold time. As part of the color-coding at 110, the first and second colors may be shaded proportionately to the difference between the respective time-to-target-replenishment of the respective color-coded pixel and the predetermined threshold time.

The first color and the second color are different from each other, such that respective pixels above and below the predetermined threshold time may be distinguished from each other by creating and displaying the output image at 112. Specifically, the creating and displaying the output image at 112 includes displaying the plurality of pixels after they have been color-coded according to the results from comparing the respective time-to-target-replenishment for each respective pixel to the predetermined threshold time at 109. The creating and displaying the output image at 112 thereby is configured to differentiate between one or more portions of the tissue experiencing time-to-target-replenishment values that are faster than the predetermined threshold time and one or more portions of the tissue experiencing time-to-target-replenishment values that are slower than the predetermined threshold time. In some methods 100, the displaying the output image at 112 may be on a monitor, a tablet, a mobile device, and/or another screen, such as a display screen of the ultrasound system.

In some examples, using the dataset to determine the time-to-target-replenishment for each respective pixel at 108 includes cropping each respective subsequent ultrasound image to a pixel grid centered on a respective pixel (e.g., pixel grids 12; see FIGS. 3A-4G), and using the respective subsequent video intensities of all the respective pixels of the pixel grid for each time point. The cropping step at 108 may then be repeated for each respective pixel of the tissue of interest.

Some methods 100 include determining at least one criterion affecting a confidence level in the time-to-target-replenishment for each respective pixel at 114. In such examples, the creating and displaying the output image at 112 may include displaying one or more respective pixels transparently if one or more of the at least one criteria is met. The at least one criterion may be, for example, a threshold level for the steady-state concentration of microbubbles in the blood volume, a threshold value for blood velocity, and/or a threshold value for the standard error of fit of a/the model used to fit the dataset. In specific, non-limiting examples, the at least one criterion may be the threshold level for the steady-state concentration of microbubbles in the blood volume being lower than 10, a threshold value of blood velocity being greater than 250, and/or a threshold value for the standard error of fit being greater than 300. Thus, the displaying one or more respective pixels transparently at 112 if one or more of the criteria determined at 114 is met may be configured to visually represent the goodness of fit of the dataset to the model.

Additionally or alternatively, methods 100 may include introducing the microbubble contrast agents into a circulatory system at 116, where the microbubble contrast agents are configured to enhance visibility of blood in the ultrasound image of tissue when the contrast agent is present in the tissue. Then, the microbubbles in the tissue may be destroyed at 118. In some methods 100, the initial video intensity of the pixels is determined prior to the destroying the microbubbles at 118 (e.g., by taking an initial ultrasound image at 122, or processing an initial ultrasound image received by the ultrasound system). In some methods 100, the initial video intensity of the pixels is determined at the time of the destroying the microbubbles at 118, or just after the destroying the microbubbles at 118. Then, a plurality of subsequent ultrasound images may be taken at 120 (or otherwise received by the system), to determine the subsequent video intensities of the pixels at 104. In some examples, at least 5-20 subsequent ultrasound images per heartbeat may be taken within 2 minutes after microbubble destruction, often resulting in a total of hundreds of images, though more or fewer subsequent ultrasound images may be taken in more or less time, in other examples. The desired images (e.g., end systolic images) may be selected from the real-time images to be used in some presently disclosed methods.

One or more steps of the various methods 100 and techniques described herein may be implemented in the context of computer-executable instructions or software that are stored in computer-readable storage and executed by the processor(s) of one or more computers, tablets, mobile devices, or other devices. Generally, program modules include routines, programs, objects, components, data structures, etc., and define operating logic for performing particular tasks or implementing particular abstract data types. As used herein, the term "module" when used in connection with software or firmware functionality may refer to code or computer program instructions that are integrated to varying degrees with the code or computer program instructions of other such "modules." The distinct nature of the different modules described and depicted herein is used for explanatory purposes and should not be used to limit the scope of this disclosure.

Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances. Similarly, software may be stored and distributed in various ways and using different means, and the particular software storage and execution configurations may be varied in many different ways. Thus, software implementing the methods and techniques described above may be distributed on various types of computer-readable media, not limited to the forms of memory that are specifically described herein.

Figure 14:
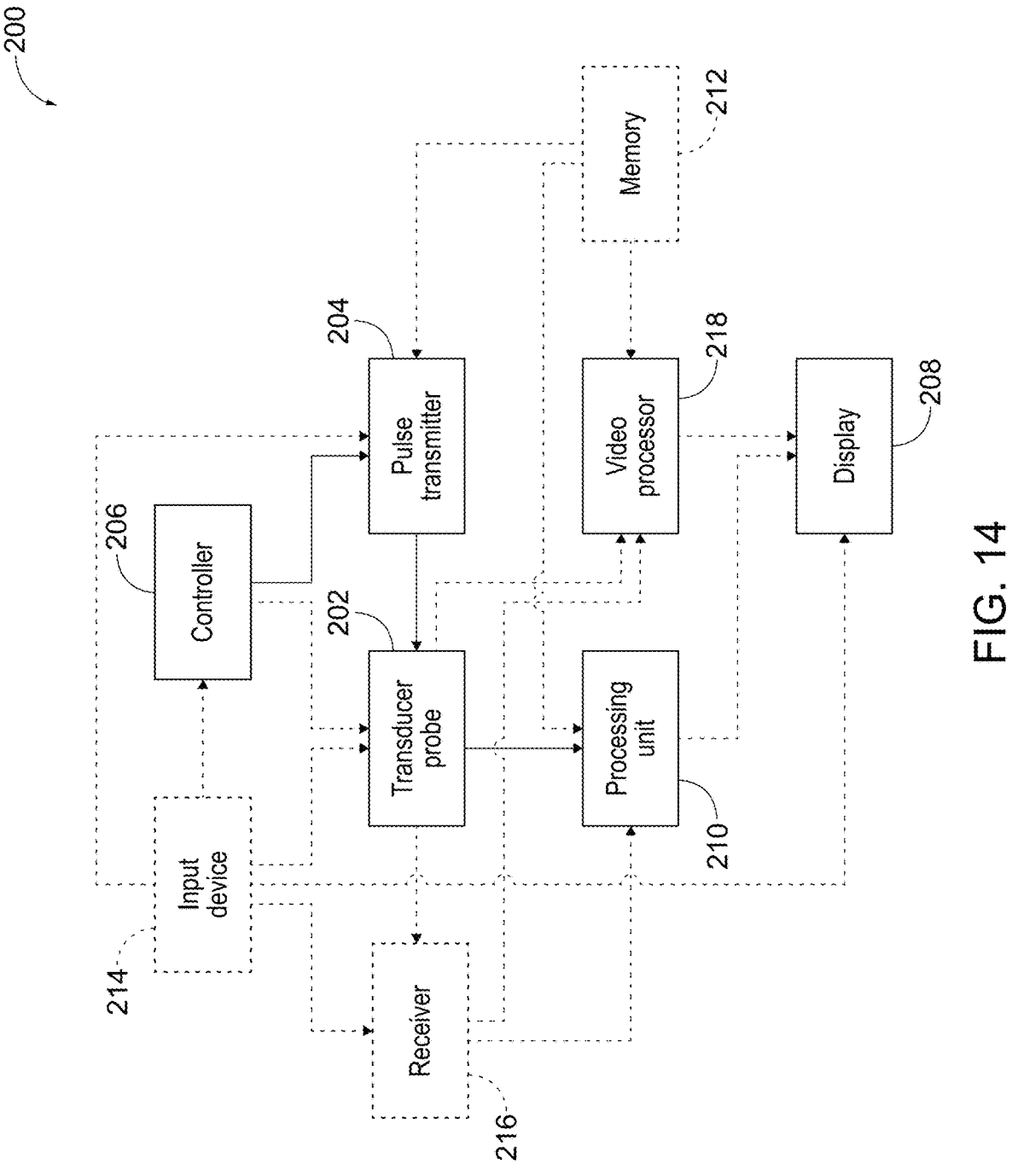
FIG. 14 is a schematic flowchart representation of illustrative, non-exclusive examples of systems for displaying blood replenishment time in a tissue, according to the present disclosure.

FIG. 14 schematically represents systems 200 that may be used to perform methods according to the present disclosure. System 200 may include an ultrasonic transducer probe 202 configured to send and receive ultrasonic waves to a tissue by converting electrical energy to acoustic pulses and vice versa, a pulse transmitter 204 configured to generate ultrasound pulses, and a controller 206 configured to control a transducer pulse emitted from ultrasonic transducer probe 202. Systems 200 also may include a display 208 configured to display one or more images from ultrasound data received from ultrasonic transducer probe 202 and processed by at least one processing unit 210. The at least one processing unit 210 may be operatively coupled to ultrasonic transducer probe 202 and responsive to temporal sequences of contrast echo signals from a plurality of respective locations in the tissue being imaged. Systems 200 also may include a memory 212 configured to store non-transitory computer-readable instructions that, when executed by the at least one processing unit 210, cause system 200 to perform the methods for displaying blood replenishment time in a tissue described herein. Memory 212 also may be configured to store still and/or video images produced based on the ultrasonic waves received by ultrasonic transducer probe 202 from the tissue. Memory 212 may be, for example, a memory of a mobile device, a tablet, and/or a computer. In some examples, memory 212 may be accessed over the internet, such as via an app. In some examples, a mobile app or other software application may be stored on non-transitory computer-readable memory of a processing unit of mobile device, tablet, laptop, or other computer system. Systems 200 thus may be configured to perform diagnostic ultrasonic imaging.

Controller 206 may be configured to change the amplitude, frequency, and/or duration of the pulses emitted from ultrasonic transducer probe 202. Systems 200 also may include an input device 214 configured to receive input from a user and take measurements from display 208. Input device 214 may, for example, be operatively coupled to controller 206, pulse transmitter 204, display 208, and/or other components of system 200 (e.g., a receiver 216) to adjust and/or provide input to any or all of these components. In some examples, systems 200 include receiver 216, configured to detect, compress, and/or amplify signals returning to ultrasonic transducer probe 202 from the tissue.

Display 208 display may be configured to display an output image (e.g., output image 30) that displays the plurality of pixels, with the plurality of pixels color-coded according to the color-coding the time-to-target-replenishment, thereby differentiating between one or more portions of the tissue experiencing time-to-target-replenishment that are below the predetermined threshold time and one or more portions of the tissue experiencing time-to-target-replenishment that are above the predetermined threshold time. In some examples, a video processor 218 is configured to create the output image. Systems 200 may be configured to process a plurality of images taken over a plurality of physiological periodic cycles (e.g., a plurality of heartbeats). Systems 200 also may be configured to record echocardiogram (ECG) signals simultaneously with the one or more images from the ultrasound data.

According to the present disclosure, the at least one processing unit 210 may be configured to execute instructions, applications, or programs stored in memory 212. In some examples, the at least one processing unit 210 includes a hardware processor that includes, without limitation, a hardware central processing unit (CPU), a graphics processing unit (GPU), a field-programmable gate array (FPGA), a complex programmable logic device (CPLD), an application-specific integrated circuit (ASIC), a system-on-chip (SoC), or a combination thereof. Memory 212 is an example of computer-readable media. Computer-readable media may include two types of computer-readable media, namely computer storage media and communication media. Computer storage media may include volatile and non-volatile media, removable and non-removable media implemented in any method or technology for storage of information such as computer-readable instructions, data structures, program modules, or other data. Computer storage media includes but is not limited to, random access memory (RAM), read-only memory (ROM), erasable programmable read-only memory (EEPROM), flash memory or other memory technology, compact disc read-only memory (CD-ROM), digital versatile disk (DVD), or other optical storage, magnetic cassettes, magnetic tape, magnetic disk storage or other magnetic storage devices, or any other non-transmission medium that may be used to store the desired information and which may be accessed by a computing device such as network-connected device, external computing device, or other computing devices that may be included in systems 200. In general, computer storage media may include computer-executable instructions that, when executed by one or more processors, cause various functions and/or operations described herein to be performed. In contrast, communication media embodies computer-readable instructions, data structures, program modules, or other data in a modulated data signal, such as a carrier wave, or other transmission mechanism. As defined herein, computer storage media does not include communication media.

Additionally, systems 200 may include one or more network interfaces that serve as physical and/or logical interfaces for connecting the respective computing device(s) to another computing device or a network. For example, network interfaces may enable WiFi-based communication such as via frequencies defined by the IEEE 802.11 standards, short-range wireless frequencies such as Bluetooth®, or any suitable wired or wireless communications protocol that enables the respective computing device to interface with other computing devices. The architectures, systems, and individual elements described herein may include many other logical, programmatic, and physical components, of which those shown in the accompanying figures are merely examples that are related to the discussion herein.

In some examples, microbubble contrast agents may be selected according to the desired use or type of tissue being imaged. For example, microbubbles may be selected based on a size of the microbubbles, a type of encapsulated gas, and/or a type or elasticity of a material that forms a microbubble shell or wall encapsulating the gas (e.g., a lipid, a protein, and/or other stabilizing surface membranes such as polymers or film-forming surfactants). The ultrasonic properties of these microbubbles are different from the ultrasonic properties of blood cells and biological tissues and generally will reflect the ultrasound source with a significant frequency increase and/or nonlinear response. The microbubble shell material may be selected to determine how easily the microbubble is taken up by the immune system, how long the microbubble remains in circulation, and/or how much acoustic energy the microbubble can withstand before bursting. In some examples, microbubble shells may be formed of albumin, galactose, lipid, and/or polymers. Additionally or alternatively, hydrophobic particles may be applied to stabilize microbubble shells. The gas or other core material within the microbubble shell may be selected based on its echogenicity (e.g., its characteristic signal) and/or the lifespan of the microbubble in circulation and may be formed of air or heavy gases, like perfluorocarbon or nitrogen. In some examples, microbubble cores may include liquids and/or solids in addition to or instead of gases. Generally, however, methods described herein may be performed with any commercially available ultrasound enhancing agent.

Microbubbles used in presently disclosed methods may have a diameter between about 1-4 micrometers. When used in human tissue such as the myocardium, microbubbles smaller in diameter than red blood cells may be selected. Specific examples of microbubble materials may include perflutren lipids, perfluorocarbon emulsions, perfluorocarbon gas, octafluoropropane encapsulated in an outer lipid shell or albumin shell, sulphur hexafluoride, perflexane lipids, polyethylene glycol, and/or targeted microbubbles that include ligands configured to bind with specific receptors expressed by cell types of interest. In some examples, any biocompatible gas may be present in the microbubbles such as nitrogen, oxygen, carbon dioxide, hydrogen, helium, argon, xenon or krypton, a sulphur fluoride such as sulphur hexafluoride, disulphur decafluoride or trifluoromethylsulphur pentafluoride, selenium hexafluoride, methylsilane, dimethylsilane, an alkane, methane, ethane, a propane, a butane, a pentane, a cycloalkane, cyclopropane, cyclobutene, cyclopentane, an alkene, ethylene, propene, propadiene, a butene, an alkyne, acetylene, propyne, an ether, dimethyl ether, a ketone, an ester, and/or a halogenated low molecular weight hydrocarbon. Suitable halogenated hydrocarbon gases may include, for example, bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1-1-difluoroethane, perfluorocarbons, perfluoroalkanes, perfluoromethane, perfluoroethane, perfluoropropanes, perfluorobutanes, perfluoro-n-butane, perfluoropentanes, perfluorohexanes, perfluoroheptanes, perfluoroalkenes, perfluoropropene, perfluorobutenes, perfluorobutadiene, perfluoroalkanes, perfluorobut-2-yne, perfluorocycloalkanes, perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane, perfluorocycloheptane, chloride, fluorinated (e.g. perfluorinated) ketones, perfluoroacetone, fluorinated ethers, and/or perfluorodiethyl ether. In some examples, the microbubble materials may be selected such that the microbubbles are sensitive to the initial ultrasound pulse(s), thereby limiting the intensity required to destroy the microbubbles.

Illustrative, non-exclusive examples of inventive subject matter according to the present disclosure are described in the following enumerated paragraphs:

A1. A method for displaying one or more parameter values in a tissue, the method comprising:

determining and/or measuring a respective initial video intensity for each respective pixel of a plurality of pixels of an ultrasound image taken at or near an initial timepoint, at which microbubble contrast agents are selectively destroyed, wherein the respective initial video intensity for each respective pixel is proportional to a concentration of microbubbles in a blood volume within a respective location of the tissue corresponding to the respective pixel at the initial timepoint;

determining and/or measuring a respective subsequent video intensity of each respective pixel of the plurality of pixels at each of a plurality of subsequent selected timepoints, using a plurality of subsequent ultrasound images taken at the plurality of subsequent selected timepoints after the initial timepoint to create a dataset;

selecting a parameter relevant to the tissue to be analyzed;

using the dataset to determine a respective steady-state concentration of microbubbles in the blood volume, a respective blood velocity, and a respective parameter value for each respective pixel of the plurality of pixels;

selecting a threshold value, wherein a respective parameter value is outside of acceptable limits when the respective parameter value is one of above the threshold value or below the threshold value, and wherein a respective parameter value is within acceptable limits when the respective parameter value is the other of above the threshold value or below the threshold value;

color-coding the parameter value for each respective pixel of the plurality of pixels using a colormap, wherein the color-coding the parameter value comprises assigning a first color of the colormap to respective parameter values that are below the threshold value, and assigning a second color of the colormap to respective parameter values that are above the threshold value, wherein the first color is different from the second color; and enhancing and adding information to the ultrasound image taken at or near an initial timepoint and the plurality of subsequent ultrasound images by creating and displaying an output image that displays the plurality of pixels, with the plurality of pixels color-coded according to the color-coding the parameter value, thereby differentiating between one or more portions of the ultrasound image corresponding to areas of the tissue experiencing parameter values that are below the threshold value and one or more portions of the ultrasound image indicating areas of the tissue parameter values that are above the threshold value.

A1.1. The method of paragraph A1, further comprising selectively destroying the microbubble contrast agents at or near the initial timepoint.

A1.2. The method of any of paragraphs A1-A1.1, further comprising selecting the subsequent selected timepoints.

A1.3. The method of any of paragraphs A1-A1.2, further comprising selecting an elapsed time between each subsequent selected timepoint of the plurality of subsequent selected timepoints using criteria particular to the tissue.

A1.4. The method of any of paragraphs A1-A1.3, further comprising selecting a suitable colormap.

A1.5. The method of any of paragraphs A1-A1.4, wherein the parameter value comprises a time-to-target-replenishment, wherein the time-to-target-replenishment is an amount of time it takes for the respective subsequent video intensity of each respective pixel of the plurality of pixels to increase from the respective initial video intensity, to a predetermined percentage of a respective video intensity corresponding to the respective steady-state concentration of microbubbles in the blood volume.

A1.6. The method of any of paragraphs A1-A1.5, wherein the selecting the parameter comprises selecting a target percentage of video intensity to be used for determining a/the time-to-target-replenishment for each respective pixel of the plurality of pixels, wherein the time-to-target-replenishment is an/the amount of time it takes for the respective subsequent video intensity of each respective pixel of the plurality of pixels to increase from the respective initial video intensity, to the target percentage of a/the respective video intensity corresponding to a/the respective steady-state concentration of microbubbles in the blood volume.

A1.7. The method of any of paragraphs A1-A1.6, wherein the selecting the threshold value comprises selecting a threshold time, above which a respective time-to-target-replenishment is outside of acceptable limits, and below which a respective time-to-target-replenishment is within acceptable limits.

A1.8. The method of any of paragraphs A1.5-A1.7, wherein the color-coding the parameter value for each respective pixel comprises color-coding respective pixels having faster respective times-to-target-replenishment that are less than the threshold time a darker shade of the first color than respective pixels having slower respective times-to-target-replenishment that are also less than the threshold time, and wherein the color-coding the time-to-target-replenishment for each respective pixel comprises color-coding respective pixels having slower respective times-to-target-replenishment are greater than the threshold time a darker shade of the second color than respective pixels having faster respective times-to-target-replenishment that are also greater than the threshold time.

A1.9. The method of any of paragraphs A1-A1.8, wherein the selecting the parameter comprises selecting a ratio of blood replenishment time under stress to blood replenishment time at rest, and determining a respective ratio for each respective pixel of the plurality of pixels; and wherein the selecting the threshold comprises selecting a threshold ratio, below which a respective ratio is outside of acceptable limits, and above which a respective ratio is within acceptable limits.

A2. The method of any of paragraphs A1-A1.9, wherein the using the dataset to determine the parameter value for each respective pixel of the plurality of pixels comprises, for each respective pixel, cropping each respective subsequent ultrasound image to a pixel grid centered on the respective pixel, and using each respective subsequent video intensity of each respective pixel of the pixel grid.

A2.1. The method of paragraph A2, wherein the pixel grid comprises a 7×7 pixel grid.

A3. The method of any of paragraphs A1-A2.1, wherein the using the dataset to determine the respective steady-state concentration of microbubbles in the blood volume, the respective blood velocity, and the respective parameter value for each respective pixel comprises fitting the dataset to a model to determine the respective steady-state concentration of microbubbles in the blood volume and the respective blood velocity, and calculating the respective parameter value based on the respective steady-state concentration of microbubbles in the blood volume.

A4. The method of any of paragraphs A1-A3, further comprising:

determining at least one criterion affecting a confidence level in the parameter value determined for each respective pixel; and displaying one or more respective pixels transparently if one or more of the at least one criterion is met.

A5. The method of paragraph A4, wherein the at least one criterion comprises a threshold level for the steady-state concentration of microbubbles in the blood volume, a threshold value for blood velocity, and/or a threshold value for the standard error of fit of a/the model used to fit the dataset.

A6. The method of paragraph A4 or A5, wherein the at least one criterion comprises a/the threshold level for the steady-state concentration of microbubbles in the blood volume being lower than 10.

A7. The method of any of paragraphs A4-A6, wherein the at least one criterion comprises a/the threshold value of blood velocity being greater than 250.

A8. The method of any of paragraphs A4-A7, wherein the at least one criterion comprises a/the threshold value for the standard error of fit being greater than 300.

A9. The method of any of paragraphs A4-A6, wherein the displaying one or more respective pixels transparently if one or more of the at least one criterion is met is configured to visually represent the goodness of fit of the dataset to a/the model.

A10. The method of any of paragraphs A1-A9, further comprising introducing the microbubble contrast agents into a circulatory system, wherein the microbubble contrast agents are configured to enhance visibility of blood in the ultrasound image of the tissue when the microbubble contrast agents are present in the tissue.

A11. The method of any of paragraphs A1-A10, further comprising destroying the microbubble contrast agents within the tissue.

A12. The method of any of paragraphs A1-A11, wherein the tissue is a myocardium.

A13. The method of any of paragraphs A1-A12, further comprising performing an ultrasound scan to obtain the ultrasound image taken at or near the initial timepoint and the plurality of subsequent ultrasound images.

A14. The method of any of paragraphs A1-A13, wherein the plurality of subsequent ultrasound images comprises at least 5-20 ultrasound images per heartbeat, taken within 2 minutes after the destroying the microbubble contract agents.

A15. The method of any of paragraphs A1-A14, further comprising, receiving from a remote location the ultrasound image taken at or near the initial timepoint and the plurality of subsequent ultrasound images.

A16. The method of any of paragraphs A1-A15, wherein the predetermined percentage is at least 50%, at least 60%, at least 70%, at least 80%, and/or at least 90%.

A17. The method of any of paragraphs A1-A16, wherein the colormap comprises a diverging colormap.

A18. The method of any of paragraphs A1-A17, further comprising selecting the colormap based on providing an intuitive distinction for a human observer to distinguish between normally and abnormally perfused regions in the ultrasound image.

A19. The method of any of paragraphs A1-A18, further comprising selecting the threshold value.

A19.1. The method of paragraph A19, wherein the threshold value comprises a predetermined threshold time.

A20. The method of paragraph A19.1, wherein the predetermined threshold time is 2 seconds for a subject under stress.

A21. The method of paragraph A19.1 or A20, wherein the predetermined threshold time is 5 seconds for the subject at rest.

A22. The method of any of paragraphs A1-A21, wherein the color-coding the parameter value for each respective pixel comprises color-coding respective pixels having a value that is faster or less than the threshold value a darker shade of the first color than respective pixels having slower or greater respective values that are also less than the threshold value.

A23. The method of any of paragraphs A1-A22, wherein the color-coding a/the parameter value for each respective pixel comprises color-coding respective pixels having slower or greater respective values than the threshold value a darker shade of the second color than respective pixels having faster or lesser respective values that are also greater than the threshold value.

A24. The method of any of paragraphs A1-A23, further comprising displaying the output image on a monitor, a tablet, a mobile device, and/or another screen.

A25. The method of any of paragraphs A1-A24, wherein one or more steps of the method are automated.

A26. The method of any of paragraphs A1-A25, wherein the method is computer-implemented.

A27. A method for displaying parameter values in a tissue, the method comprising:

injecting microbubble contrast agents into a subject's bloodstream;

delivering a high-energy pulse to selectively destroy microbubble contrast agents within the tissue;

taking an ultrasound image at or near an initial timepoint, at which the microbubble contrast agents are selectively destroyed;

taking a plurality of subsequent ultrasound images at a plurality of subsequent selected timepoints after the initial timepoint to create a dataset;

measuring a respective initial video intensity for each respective pixel of a plurality of pixels of the ultrasound image taken at or near the initial timepoint, wherein the respective initial video intensity for each respective pixel is proportional to a concentration of microbubbles in a blood volume within the tissue in a respective location of the tissue corresponding to the respective pixel at the initial timepoint;

measuring a respective subsequent video intensity of each respective pixel of the plurality of pixels at each of the plurality of subsequent selected timepoints, using the plurality of subsequent ultrasound images;

selecting a parameter relevant to the tissue;

using the dataset to determine a respective steady-state concentration of microbubbles in the blood volume, a respective blood velocity, and a respective measure of the parameter;

selecting a suitable colormap;

color-coding each respective pixel of the plurality of pixels using the colormap, wherein the color-coding comprises assigning a first color of the colormap to respective parameter values that are below a predetermined threshold, and assigning a second color of the colormap to respective parameter values that are above the predetermined threshold, wherein the first color is different from the second color; and enhancing and adding information to the ultrasound image taken at or near an initial timepoint and the plurality of subsequent ultrasound images by creating and displaying an output image that displays the plurality of pixels, with the plurality of pixels color-coded, thereby differentiating between one or more portions of the ultrasound image indicating corresponding areas of the tissue experiencing parameter values that are below the predetermined threshold, and one or more portions of the ultrasound image indicating areas of the tissue experiencing parameter values that are above the predetermined threshold.

B1. A system for processing blood replenishment time in a tissue, the system comprising:

an ultrasonic transducer probe configured to send and receive ultrasonic waves to the tissue by converting electrical energy to acoustic pulses and vice versa;

a pulse transmitter configured to generate pulse echoes in brief bursts;

a controller configured to control a transducer pulse emitted from the ultrasonic transducer probe;

a display configured to display one or more images from ultrasound data received from the ultrasonic transducer probe and processed by a processing unit;

at least one processing unit operatively coupled to the ultrasonic transducer probe and responsive to temporal sequences of contrast echo signals from a plurality of respective locations in the tissue; and a memory, storing non-transitory computer-readable instructions that, when executed by the at least one processing unit, cause the system to perform the method of any of paragraphs A1-A27.

B2. The system according to paragraph B1, wherein the system is configured to perform diagnostic ultrasound imaging.

B3. The system according to any of paragraphs B1-B2, wherein the controller is configured to change amplitude, frequency, and/or duration of the acoustic pulses emitted from the ultrasonic transducer probe.

B4. The system according to any of paragraphs B1-B3, further comprising an input device configured to receive input from a user and take measurements from the display.

B5. The system according to any of paragraphs B1-B4, wherein the memory is configured to store still images and video images produced based on the ultrasonic waves received by the ultrasonic transducer probe from the tissue.

B6. The system according to any of paragraphs B1-B5, further comprising a receiver configured to detect, compress, and/or amplify signals returning to the ultrasonic transducer probe.

B7. The system according to any of paragraphs B1-B6, wherein the display is further configured to display an output image that displays a plurality of pixels, with the plurality of pixels color-coded according to their respective parameter value, thereby differentiating between one or more portions of the tissue experiencing respective parameter values that are below a threshold value and one or more portions of the tissue experiencing respective parameter values that are above the threshold value.

B8. The system according to any of paragraphs B1-B7, further comprising a video processor configured to create an/the output image.

B9. The system according to any of paragraphs B1-B8, wherein the system is configured to process a plurality of images taken over a plurality of physiological periodic cycles.

B10. The system according to any of paragraphs B1-B9, wherein the system is configured to record electrocardiogram (ECG) signals simultaneously with the one or more images from the ultrasound data.

C1. A computer-readable medium configured for processing and displaying blood replenishment time in a tissue, wherein the computer-readable medium is configured to perform the method of any of paragraphs A1-A27.

C2. The computer-readable medium of paragraph C1, configured to store a series of programmable instructions for performing the method of any of paragraphs A1-A27.

D1. Use of the system of any of paragraphs B1-B10 to perform diagnostic ultrasound imaging.

D2. The use of the system of any of paragraphs B1-B10 to perform myocardial contrast echocardiography.

D3. The use of the system of any of paragraphs B1-B10 to perform the method of any of paragraphs A1-A27.

D4. The use of the system of any of paragraphs B1-B10 to display an output image that displays a plurality of pixels from an ultrasound image of a tissue, with the plurality of pixels color-coded according to a color-coding of a parameter value of each respective pixel of the plurality of pixels, thereby differentiating between one or more portions of the tissue experiencing respective parameter values that are below a threshold value and one or more portions of the tissue experiencing respective parameter values that are above the threshold value.

D5. The use according to paragraph D4, wherein the parameter value comprises a time-to-target-replenishment, and wherein the time-to-target-replenishment is an amount of time it takes for a respective subsequent video intensity of each respective pixel of the plurality of pixels to increase from a respective initial video intensity, to a predetermined percentage of a respective steady-state video intensity corresponding to a respective steady-state concentration of microbubbles in the blood volume.

D6. The use of the computer-readable medium of any of paragraphs C1-C2 to perform diagnostic ultrasound imaging.

D7. The use of the computer-readable medium of any of paragraphs C1-C2 to perform myocardial contrast echocardiography.

D8. The use of the computer-readable medium of any of paragraphs C1-C2 to perform the method of any of paragraphs A1-A27.

D9. The use of the computer-readable medium of any of paragraphs C1-C2 to display an output image that displays a plurality of pixels from an ultrasound image of a tissue, with the plurality of pixels color-coded according to a color-coding of an time-to-target-replenishment of each respective pixel of the plurality of pixels, thereby differentiating between one or more portions of the tissue experiencing respective times-to-target-replenishment that are below a predetermined threshold time and one or more portions of the tissue experiencing respective times-to-target-replenishment that are above the predetermined threshold time, wherein the time-to-target-replenishment is the amount of time it takes for a respective subsequent video intensity of each respective pixel of the plurality of pixels to increase from a respective initial video intensity to a predetermined percentage of a respective steady-state video intensity corresponding to a respective steady-state concentration of microbubbles in the blood volume.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" may mean A alone, B alone, C alone, A and B together, A and C together, B and C together, or A, B, and C together, and optionally any of the above in combination with at least one other entity.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, a mobile device may be any suitable device or devices that are configured to perform the functions of the mobile device discussed herein. For example, the mobile device may include one or more of an electronic controller, a dedicated controller, a special-purpose controller, a personal computer, a mobile phone, a special-purpose computer, a display device, a logic device, a memory device, and/or a memory device having computer readable media suitable for storing computer-executable instructions for implementing aspects of systems, methods, and/or mobile apps according to the present disclosure.

A controller may be any suitable device or devices that are configured to perform the functions of the controller discussed herein. For example, the controller may include one or more of an electronic controller, a dedicated controller, a special-purpose controller, a personal computer, a special-purpose computer, a display device, a logic device, a memory device, and/or a memory device having computer readable media suitable for storing computer-executable instructions for implementing aspects of systems and/or methods according to the present disclosure.

Additionally or alternatively, mobile devices, tablets, computers, etc. may be configured to read non-transitory computer readable storage, or memory, media suitable for storing computer-executable instructions, or software, for implementing methods or steps of methods according to the present disclosure. Examples of such media include CD-ROMs, disks, hard drives, flash memory, etc. As used herein, storage, or memory, devices and media having computer-executable instructions as well as computer-implemented methods and other methods according to the present disclosure are considered to be within the scope of subject matter deemed patentable in accordance with Section 101 of Title 35 of the United States Code.

The invention claimed is:

1. A method for displaying parameter values in a tissue, the method comprising:
measuring a respective initial video intensity for each respective pixel of a plurality of pixels of an ultrasound image taken at or near an initial timepoint, at which microbubble contrast agents are selectively destroyed, wherein the respective initial video intensity for each respective pixel is proportional to a concentration of microbubbles in a blood volume within a respective location of the tissue corresponding to the respective pixel at the initial timepoint;

measuring a respective subsequent video intensity of each respective pixel of the plurality of pixels at each of a plurality of subsequent selected timepoints, using a plurality of subsequent ultrasound images taken at the plurality of subsequent selected timepoints after the initial timepoint to create a dataset;

selecting a parameter relevant to the tissue to be analyzed, wherein the selecting the parameter comprises selecting a ratio of blood replenishment time under stress to blood replenishment time at rest, and determining a respective ratio for each respective pixel of the plurality of pixels;

using the dataset to determine a respective steady-state concentration of microbubbles in the blood volume, a respective blood velocity, and a respective parameter value for each respective pixel of the plurality of pixels;

selecting a threshold value, wherein a respective parameter value is outside of normal or acceptable limits when the respective parameter value is one of above the threshold value or below the threshold value, wherein a respective parameter value is within acceptable limits when the respective parameter value is the other of above the threshold value or below the threshold value, and wherein the selecting the threshold value comprises selecting a threshold ratio below which a respective ratio is outside of acceptable limits, and above which a respective ratio is within acceptable limits;

selecting a colormap;

color-coding the parameter value for each respective pixel of the plurality of pixels using the colormap, wherein the color-coding the parameter value comprises assigning a first color of the colormap to respective parameter values that are below the threshold value, and assigning a second color of the colormap to respective parameter values that are above the threshold value, wherein the first color is different from the second color; and enhancing and adding information to the ultrasound image taken at or near an initial timepoint and the plurality of subsequent ultrasound images by creating and displaying an output image that displays the plurality of pixels, with the plurality of pixels color-coded according to the color-coding the parameter value, thereby differentiating between one or more portions of the ultrasound image indicating areas of the tissue experiencing parameter values that are below the threshold value and one or more portions of the ultrasound image indicating areas of the tissue experiencing parameter values that are above the threshold value.

2. The method according to claim 1, wherein the selecting the parameter comprises selecting a target percentage of video intensity to be used for determining a time-to-target-replenishment for each respective pixel of the plurality of pixels, wherein the time-to-target-replenishment is an amount of time it takes for the respective subsequent video intensity of each respective pixel of the plurality of pixels to increase from the respective initial video intensity to the target percentage of a respective video intensity corresponding to a respective steady-state concentration of microbubbles in the blood volume; and wherein the selecting the threshold value comprises selecting a threshold time above which a respective time-to-target-replenishment is outside of acceptable limits, and below which a respective time-to-target-replenishment is within acceptable limits.

3. The method according to claim 2, wherein the color-coding the parameter value for each respective pixel comprises color-coding respective pixels having faster respective times-to-target-replenishment that are less than the threshold time a darker shade of the first color than respective pixels having slower respective times-to-target-replenishment that are also less than the threshold time, and wherein the color-coding the time-to-target-replenishment for each respective pixel comprises color-coding respective pixels having slower respective times-to-target-replenishment are greater than the threshold time a darker shade of the second color than respective pixels having faster respective times-to-target-replenishment that are also greater than the threshold time.

4. The method according to claim 2, wherein the using the dataset to determine the respective steady-state concentration of microbubbles in the blood volume, the respective blood velocity, and the respective parameter value for each respective pixel comprises fitting the dataset to a model to determine the respective steady-state concentration of microbubbles in the blood volume and the respective blood velocity, and calculating the respective parameter value based on the respective steady-state concentration of microbubbles in the blood volume.

5. The method according to claim 2, further comprising:

determining at least one criterion affecting a confidence level in the time-to-target-replenishment determined for each respective pixel; and displaying one or more respective pixels transparently if one or more of the at least one criterion is met, thereby visually representing the goodness of fit of the dataset to a model.

6. The method according to claim 1, wherein the tissue is a myocardium.

7. The method according to claim 1, wherein the plurality of subsequent ultrasound images comprises at least 5-20 ultrasound images per heartbeat, taken within 2 minutes after the destroying the microbubble contrast agents.

8. The method according to claim 1, wherein the colormap comprises a diverging colormap.

9. The method according to claim 1, wherein the threshold value is 2 seconds for a subject under stress, and wherein the threshold value is 5 seconds for a subject at rest.

10. The method according to claim 1, further comprising selecting an elapsed time between each of the plurality of subsequent selected timepoints, using criteria particular to the tissue.

11. A system for processing blood replenishment time in a tissue, the system comprising:

an ultrasonic transducer probe configured to send and receive ultrasonic waves to the tissue by converting electrical energy to acoustic pulses and vice versa;

a pulse transmitter configured to generate pulse echoes in brief bursts;

a controller configured to control a transducer pulse emitted from the ultrasonic transducer probe;

a display configured to display one or more images from ultrasound data received from the ultrasonic transducer probe and processed by a processing unit;

at least one processing unit operatively coupled to the ultrasonic transducer probe and responsive to temporal sequences of contrast echo signals from a plurality of respective locations in the tissue; and a memory storing non-transitory computer-readable instructions that, when executed by the at least one processing unit, cause the system to perform the method according to claim 1.

12. The system according to claim 11, wherein the display is further configured to display an output image that displays a plurality of pixels, with the plurality of pixels color-coded according to their respective parameter values, thereby differentiating between one or more portions of the ultrasound image indicating areas of the tissue experiencing respective parameter values that are below the threshold value and one or more portions of the ultrasound image indicating areas of the tissue experiencing respective times-to-target-replenishment that are above the threshold value.

13. The system according to claim 12, further comprising a video processor configured to create the output image.

14. The system according to claim 11, wherein the system is configured to process a plurality of images taken over a plurality of physiological periodic cycles.

15. The system according to claim 11, wherein the system is configured to record electrocardiogram (ECG) signals simultaneously with the one or more images from the ultrasound data.

16. A computer-readable medium configured for processing and displaying blood replenishment time in a tissue, wherein the computer-readable medium is configured to perform the method according to claim 1.

17. A computer-readable medium configured for processing and displaying blood replenishment time in a tissue, wherein in the computer-readable medium is configured to store a series of programmable instructions for performing the method according to claim 1.

18. A method for displaying parameter values in a tissue, the method comprising:

measuring a respective initial video intensity for each respective pixel of a plurality of pixels of an ultrasound image taken at or near an initial timepoint, at which microbubble contrast agents are selectively destroyed, wherein the respective initial video intensity for each respective pixel is proportional to a concentration of microbubbles in a blood volume within a respective location of the tissue corresponding to the respective pixel at the initial timepoint;

measuring a respective subsequent video intensity of each respective pixel of the plurality of pixels at each of a plurality of subsequent selected timepoints, using a plurality of subsequent ultrasound images taken at the plurality of subsequent selected timepoints after the initial timepoint to create a dataset;

selecting a parameter relevant to the tissue to be analyzed, wherein the selecting the parameter comprises selecting a target percentage of video intensity to be used for determining a time-to-target-replenishment for each respective pixel of the plurality of pixels, wherein the time-to-target-replenishment is an amount of time it takes for the respective subsequent video intensity of each respective pixel of the plurality of pixels to increase from the respective initial video intensity to the target percentage of a respective video intensity corresponding to a respective steady-state concentration of microbubbles in the blood volume;

using the dataset to determine a respective steady-state concentration of microbubbles in the blood volume;

using the dataset to determine a respective blood velocity;

using the dataset to determine a respective parameter value for each respective pixel of the plurality of pixels, wherein the respective parameter value is the time-to-target replenishment, and wherein the using the dataset to determine the respective parameter value for each respective pixel of the plurality of pixels comprises, for each respective pixel, cropping each respective subsequent ultrasound image to a pixel grid centered on the respective pixel, and using each respective subsequent video intensity of each respective pixel of the pixel grid;

selecting a threshold value, wherein a respective parameter value is outside of normal or acceptable limits when the respective parameter value is one of above the threshold value or below the threshold value, wherein a respective parameter value is within acceptable limits when the respective parameter value is the other of above the threshold value or below the threshold value, wherein the selecting the threshold value comprises selecting a threshold time above which a respective time-to-target-replenishment is outside of acceptable limits, and below which a respective time-to-target-replenishment is within acceptable limits;

selecting a colormap;

color-coding the parameter value for each respective pixel of the plurality of pixels using the colormap, wherein the color-coding the parameter value comprises assigning a first color of the colormap to respective parameter values that are below the threshold value, and assigning a second color of the colormap to respective parameter values that are above the threshold value, wherein the first color is different from the second color; and enhancing and adding information to the ultrasound image taken at or near an initial timepoint and the plurality of subsequent ultrasound images by creating and displaying an output image that displays the plurality of pixels, with the plurality of pixels color-coded according to the color-coding the parameter value, thereby differentiating between one or more portions of the ultrasound image indicating areas of the tissue experiencing parameter values that are below the threshold value and one or more portions of the ultrasound image indicating areas of the tissue experiencing parameter values that are above the threshold value.

19. A method for displaying parameter values in a tissue, the method comprising:

injecting microbubble contrast agents into a subject's bloodstream;

delivering a high-energy pulse to selectively destroy microbubble contrast agents within the tissue;

taking an ultrasound image at or near an initial timepoint at which the microbubble contrast agents are selectively destroyed;

taking a plurality of subsequent ultrasound images at a plurality of subsequent selected timepoints after the initial timepoint to create a dataset;

measuring a respective initial video intensity for each respective pixel of a plurality of pixels of the ultrasound image taken at or near the initial timepoint, wherein the respective initial video intensity for each respective pixel is proportional to a concentration of microbubbles in a blood volume within the tissue in a respective location of the tissue corresponding to the respective pixel at the initial timepoint;

measuring a respective subsequent video intensity of each respective pixel of the plurality of pixels at each of the plurality of subsequent selected timepoints, using the plurality of subsequent ultrasound images;

selecting a parameter relevant to the tissue;

using the dataset to determine a respective steady-state concentration of microbubbles in the blood volume, a respective blood velocity, and a respective measure of the parameter;

selecting a colormap;

color-coding each respective pixel of the plurality of pixels using the colormap, wherein the color-coding comprises assigning a first color of the colormap to respective parameter values that are below a predetermined threshold value, and assigning a second color of the colormap to respective parameter values that are above the predetermined threshold value, wherein the first color is different from the second color, wherein the predetermined threshold value is 2 seconds for a subject under stress, and wherein the predetermined threshold value is 5 seconds for a subject at rest; and enhancing and adding information to the ultrasound image taken at or near an initial timepoint and the plurality of subsequent ultrasound images by creating and displaying an output image that displays the plurality of pixels with the plurality of pixels color-coded, thereby differentiating between one or more portions of the ultrasound image indicating areas of the tissue experiencing parameter values that are below the predetermined threshold, and one or more portions of the ultrasound image indicating areas of the tissue experiencing parameter values that are above the predetermined threshold.

20. A method for displaying parameter values in a tissue, the method comprising:

measuring a respective initial video intensity for each respective pixel of a plurality of pixels of an ultrasound image taken at or near an initial timepoint, at which microbubble contrast agents are selectively destroyed, wherein the respective initial video intensity for each respective pixel is proportional to a concentration of microbubbles in a blood volume within a respective location of the tissue corresponding to the respective pixel at the initial timepoint;

measuring a respective subsequent video intensity of each respective pixel of the plurality of pixels at each of a plurality of subsequent selected timepoints, using a plurality of subsequent ultrasound images taken at the plurality of subsequent selected timepoints after the initial timepoint to create a dataset, wherein the plurality of subsequent ultrasound images comprises at least 5-20 ultrasound images per heartbeat, taken within 2 minutes after the destroying the microbubble contrast agents;

selecting a parameter relevant to the tissue to be analyzed;

using the dataset to determine a respective steady-state concentration of microbubbles in the blood volume, a respective blood velocity, and a respective parameter value for each respective pixel of the plurality of pixels;

selecting a threshold value, wherein a respective parameter value is outside of normal or acceptable limits when the respective parameter value is one of above the threshold value or below the threshold value, and wherein a respective parameter value is within acceptable limits when the respective parameter value is the other of above the threshold value or below the threshold value;

selecting a colormap;

color-coding the parameter value for each respective pixel of the plurality of pixels using the colormap, wherein the color-coding the parameter value comprises assigning a first color of the colormap to respective parameter values that are below the threshold value, and assigning a second color of the colormap to respective parameter values that are above the threshold value, wherein the first color is different from the second color; and enhancing and adding information to the ultrasound image taken at or near an initial timepoint and the plurality of subsequent ultrasound images by creating and displaying an output image that displays the plurality of pixels, with the plurality of pixels color-coded according to the color-coding the parameter value, thereby differentiating between one or more portions of the ultrasound image indicating areas of the tissue experiencing parameter values that are below the threshold value and one or more portions of the ultrasound image indicating areas of the tissue experiencing parameter values that are above the threshold value.

* * * * *